(12) United States Patent
Hitchcock et al.

(10) Patent No.: US 10,179,783 B2
(45) Date of Patent: Jan. 15, 2019

(54) TETRAHYDROPYRIDOPYRAZINES AS MODULATORS OF GPR6

(71) Applicant: Takeda Pharmaceutical Company Limited, Osaka (JP)

(72) Inventors: Stephen Hitchcock, San Diego, CA (US); Maria Hopkins, San Diego, CA (US); Shota Kikuchi, San Diego, CA (US); Holger Monenschein, San Diego, CA (US); Holly Reichard, San Diego, CA (US); Huikai Sun, San Diego, CA (US); Todd Macklin, Brooklyn Park, MN (US)

(73) Assignee: Taketa Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/118,447

(22) PCT Filed: Feb. 13, 2015

(86) PCT No.: PCT/US2015/015789
§ 371 (c)(1),
(2) Date: Aug. 11, 2016

(87) PCT Pub. No.: WO2015/123505
PCT Pub. Date: Aug. 20, 2015

(65) Prior Publication Data
US 2017/0174677 A1   Jun. 22, 2017

Related U.S. Application Data

(60) Provisional application No. 61/940,176, filed on Feb. 14, 2014.

(51) Int. Cl.
*C07D 471/04*   (2006.01)

(52) U.S. Cl.
CPC .................. *C07D 471/04* (2013.01)

(58) Field of Classification Search
CPC .................................................. C07D 471/04
See application file for complete search history.

(56) References Cited

U.S. PATENT DOCUMENTS 9,487,526 B2 * 11/2016 Hitchcock ............ C07D 241/44
9,770,452 B2 *  9/2017 Hitchcock ............ C07D 241/44

FOREIGN PATENT DOCUMENTS

| WO | 2006/039718 A2 | 4/2006 |
|---|---|---|
| WO | 2007023186 A1 | 3/2007 |
| WO | 2007125405 A2 | 11/2007 |
| WO | 2008127594 A2 | 10/2008 |
| WO | 2008149163 A2 | 12/2008 |
| WO | 2009021083 A1 | 2/2009 |
| WO | 2010143170 A2 | 12/2010 |
| WO | 2011150156 A2 | 12/2011 |
| WO | 2012/042539 A2 | 4/2012 |
| WO | 2012/167423 A1 | 12/2012 |
| WO | 2012167733 A1 | 12/2012 |
| WO | 2013169964 A1 | 11/2013 |
| WO | 2014/028479 A1 | 2/2014 |

OTHER PUBLICATIONS

Sekhar, et al., "Design, synthesis, and preliminary in vitro and invov pharmacological evaluation of 4-{4-[2-(4-(2-substitutedquinoxalin-3-yl)p iperazin-1-yl)ethyl]phenyl}thiazoles as atypical antipsychotic agents", Medicinal Chemistry Research (2013), vol. 22, pp. 1660-1673.
PCT, PCT/US2015/015789, "International Search Report", dated May 4, 2015, 4 pages.

* cited by examiner

*Primary Examiner* — Kahsay Habte
(74) *Attorney, Agent, or Firm* — Matthew J. Russo; David M. Stemerick

(57) ABSTRACT

The present invention provides compounds of formula I:

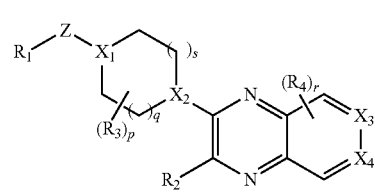

which are useful as modulators of GPR6, pharmaceutical compositions thereof, methods for treatment of conditions associated with GPR6, processes for making the compounds and intermediates thereof.

8 Claims, No Drawings

TETRAHYDROPYRIDOPYRAZINES AS MODULATORS OF GPR6

CROSS-REFERENCE TO RELATED APPLICATIONS

This application is the U.S. National Stage entry under 35 U.S.C. § 371(c) of International Application PCT/US2015/015789, filed Feb. 13, 2015, which claims the benefit of U.S. Provisional Application No. 61/940,176, filed Feb. 14, 2014.

FIELD OF THE INVENTION

The present invention relates to medicinal chemistry, pharmacology, and medicine.

BACKGROUND OF THE INVENTION

The present invention provides compounds that are G-Protein-Coupled Receptor 6 (hereinafter referred to as GPR6) modulators. GPR6 is GPCR that signals via the Gs pathway. GPR6 receptors are highly expression in the central nervous system (CNS), particularly medium spiny neurons (MSNs) of the striatum, with minimal expression in peripheral tissues. The major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors. GPR6 is enriched in D2 receptor expressing MSNs in the striatum where GPR6 activity is functionally opposed to D2 receptor signaling. Antagonism or inverse agonism of Gs coupled GPR6 decreases cAMP in MSNs and provides a functional alternative to dopamine mediated activation of D2 receptors. Therefore, the compounds of the present invention are useful to treat a variety of neurological and psychiatric disorders, including Parkinson's disease.

SUMMARY OF THE INVENTION

The present invention provides a compound of formula I:

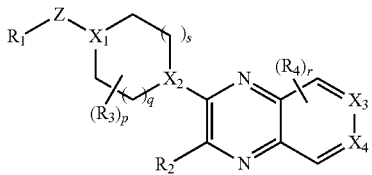

I wherein
$R_1$ is selected from the group consisting of optionally substituted $C_{3-8}$ cycloalkyl, optionally substituted $C_{3-6}$ heterocyclyl, optionally substituted $C_{6-10}$ aryl, and optionally substituted $C_{1-10}$ heteroaryl;
$X_1$ is N and $X_2$ is CH; or
$X_1$ is CH and $X_2$ is N; or
$X_1$ is N and $X_2$ is N;
when $X_1$ is N, Z is selected from the group consisting of $C_{1-6}$ alkylene, $C_{1-6}$ haloalkylene, —C(O)—, and —S(O)$_2$—;
when $X_1$ is CH, Z is selected from the group consisting of $C_{1-6}$ alkylene, $C_{1-6}$ haloalkylene, —O—, —C(O)—, —NH—, —S—, —S(O)—, and —S(O)$_2$—;
q is 0, 1, or 2;
s is 0, 1, or 2;
$R_2$ is —OR$_5$ or —NR$_6$R$_7$;
$R_3$, each time taken, is independently selected from the group consisting of $C_{1-6}$ alkyl, $C_{3-8}$ cycloalkyl, and trifluoromethyl;
p is 0, 1, or 2;
$R_4$, each time taken, is independently selected from the group consisting of $C_{1-6}$ alkyl, hydroxy, and halo;
r is 0 or 1;
$R_5$ is selected from the group consisting of $C_{1-6}$ alkyl and $C_{3-8}$ cycloalkyl;
$R_6$ is selected from the group consisting of hydrogen and $C_{1-6}$ alkyl;
$R_7$ is selected from the group consisting of optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;
$X_3$ is CCH$_3$ and $X_4$ is N; or
$X_3$ is N and $X_4$ is CCH$_3$;
excluding the compounds: N-cyclopropyl-3-(4-(2,4-difluorobenzyl)piperazin-1-yl)-7-methylpyrido[3,4-b]pyrazin-2-amine, 3-(4-(5-chloro-2-fluorobenzyl)piperazin-1-yl)-N-cyclopropyl-7-methylpyrido[3,4-b]pyrazin-2-amine, N-cyclopropyl-3-(4-(2,4-difluorobenzyl)piperidin-1-yl)-7-methylpyrido[3,4-b]pyrazin-2-amine, N-cyclopropyl-2-(4-(2,4-difluorobenzyl)piperidin-1-yl)-7-methylpyrido[3,4-b]pyrazin-3-amine, (1-(2-(cyclopropylamino)-7-methylpyrido[3,4-b]pyrazin-3-yl)piperidin-4-yl)(2,5-difluorophenyl)methanone, N-cyclopropyl-3-(4-(2,4-difluorophenoxy)piperidin-1-yl)-7-methylpyrido[3,4-b]pyrazin-2-amine, N-cyclopropyl-3-(4-((2,5-difluorophenyl)fluoromethyl)piperidin-1-yl)-7-methylpyrido[3,4-b]pyrazin-2-amine, (S)—N-cyclopropyl-3-(4-((2,5-difluorophenyl)fluoromethyl)piperidin-1-yl)-7-methylpyrido[3,4-b]pyrazin-2-amine, 3-(4-(4-chloro-2-fluorophenoxy)piperidin-1-yl)-N-cyclopropyl-7-methylpyrido[3,4-b]pyrazin-2-amine, 1-((1-(2-(cyclopropylamino)-7-methylpyrido[3,4-b]pyrazin-3-yl)piperidin-4-yl)methyl)-4-fluoropyridin-2(1H)-one, (R)—N-cyclopropyl-3-(4-((2,5-difluorophenyl)fluoromethyl)piperidin-1-yl)-7-methylpyrido[3,4-b]pyrazin-2-amine, N-cyclopropyl-3-(4-((2,4-difluorophenyl)fluoromethyl)piperidin-1-yl)-7-methylpyrido[3,4-b]pyrazin-2-amine, (R)—N-cyclopropyl-3-(4-((2,4-difluorophenyl)fluoromethyl)piperidin-1-yl)-7-methylpyrido[3,4-b]pyrazin-2-amine, (S)—N-cyclopropyl-3-(4-((2,4-difluorophenyl)fluoromethyl)piperidin-1-yl)-7-methylpyrido[3,4-b]pyrazin-2-amine, 3-(4-((5-chloro-2-fluorophenyl)difluoromethyl)piperidin-1-yl)-N-cyclopropyl-7-methylpyrido[3,4-b]pyrazin-2-amine, 5-chloro-1-((1-(2-(cyclopropylamino)-7-methylpyrido[3,4-b]pyrazin-3-yl)piperidin-4-yl)methyl)pyridin-2(1H)-one, N-cyclopropyl-3-(4-((2,5-difluorophenyl)difluoromethyl)piperidin-1-yl)-7-methylpyrido[3,4-b]pyrazin-2-amine, N-cyclopropyl-3-(4-((4-fluorophenyl)sulfonyl)piperidin-1-yl)-7-methylpyrido[3,4-b]pyrazin-2-amine, and N-cyclopropyl-3-(1-(2,4-difluorobenzyl)piperidin-4-yl)-7-methylpyrido[3,4-b]pyrazin-2-amine;
or a pharmaceutically acceptable salt thereof.

The present invention also provides pharmaceutical compositions, comprising: a compound of formula I or a pharmaceutically acceptable salt thereof and a pharmaceutically acceptable excipient.

The compounds of the present invention are modulators of GPR6 and are useful to treat a variety of neurological and psychiatric disorders, for example movement disorders including Parkinson's disease, levodopa induced dyskinesias, and Huntington's disease, drug addiction, eating disorders, cognitive disorders, schizophrenia, bipolar disorders, and depression. Thus, the present invention also provides methods of treating the conditions associated with GPR6 described herein comprising, administering to a patient in need thereof an effective amount of the compounds of the invention. The present invention provides for the use of the compounds of the invention as a medicament, including for treatment of the conditions associated with GPR6 described herein, and including for the manufacture of a medicament for treating the conditions associated with GPR6 described herein.

The present invention also provides processes from making GPR6 modulators and intermediates thereof.

DETAILED DESCRIPTION OF THE INVENTION

The term "$C_{1-4}$ alkyl" refers to a straight or branched alkyl chain of one to four carbon atoms.

The term "optionally substituted $C_{1-4}$ alkyl" refers to a $C_{1-4}$ alkyl optionally substituted with 1 to 6 substituents independently selected from the group consisting of optionally substituted $C_{1-4}$ alkoxy, $C_{1-4}$ thioalkoxy, $C_{1-9}$ amide, $C_{1-7}$ amido, amino, $C_{1-8}$ alkylamino, $C_{1-5}$ oxycarbonyl, $C_{1-5}$ carbonyloxy, $C_{1-8}$ sulfonyl, cyano, optionally substituted $C_{3-8}$ cycloalkyl, $C_{3-8}$ cycloalkoxy, halo, hydroxy, nitro, oxo, optionally substituted $C_{3-6}$ heterocyclyl, optionally substituted $C_{1-10}$ heteroaryl, and optionally substituted $C_{6-10}$ aryl.

More particularly "optionally substituted $C_{1-4}$ alkyl" refers to a $C_{1-4}$ alkyl optionally substituted with 1 to 6 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-4}$ alkyl" refers to a $C_{1-4}$ alkyl optionally substituted with 1 to 6 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-6}$ alkyl" refers to a straight or branched alkyl chain of one to six carbon atoms.

The term "optionally substituted $C_{1-6}$ alkyl" refers to a $C_{1-6}$ alkyl optionally substituted with 1 to 7 substituents independently selected from the group consisting of amino, $C_{1-8}$ alkylamino, optionally substituted $C_{1-4}$ alkoxy, $C_{1-4}$ thioalkoxy, $C_{1-9}$ amide, $C_{1-7}$ amido, $C_{1-5}$ oxycarbonyl, $C_{1-5}$ carbonyloxy, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocyclyl, and optionally substituted $C_{6-10}$ aryl.

More particularly "optionally substituted $C_{1-6}$ alkyl" refers to a $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-6}$ alkyl" refers to a $C_{1-6}$ alkyl optionally substituted with 1 to 7 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-6}$ haloalkyl" refers to a straight or branched alkyl chain of one to six carbon atoms substituted with 1 to 3 halogen atoms. More particularly, the term "$C_{1-6}$ haloalkyl" refers fluoromethyl and difluoromethyl.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-6}$ alkylene" refers to a straight or branched, divalent, alkylene chain of one to six carbon atoms.

The term "$C_{1-6}$ haloalkylene" refers to a straight or branched, divalent, alkylene chain of one to six carbon atoms substituted with 1 to 3 halogen atoms. More particularly, the term "$C_{1-6}$ haloalkylene" refers fluoromethylene and difluoromethylene.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally substituted with 1 to 6 substituents independently selected from the group consisting of $C_{1-4}$ alkoxy, $C_{1-9}$ amide, $C_{1-5}$ oxycarbonyl, cyano, optionally substituted $C_{3-8}$ cycloalkyl, halo, hydroxy, optionally substituted $C_{1-10}$ heteroaryl, and optionally substituted $C_{6-10}$ aryl. While it is understood that where the optional substituent is $C_{1-4}$ alkoxy or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

More particularly "optionally substituted $C_{1-4}$ alkoxy" refers to a $C_{1-4}$ alkoxy optionally substituted with 1 to 6 substituents independently selected from the group consisting of $C_{1-4}$ alkoxy, cyano, $C_{3-8}$ cycloalkyl, halo, hydroxy, and optionally substituted phenyl. Even more particularly "optionally substituted $C_{1-4}$ alkoxy" refers to trifluoromethoxy, difluoromethoxy, and fluoromethoxy.

The term "$C_{1-9}$ amide" refers to a —C(O)NR$_a$R$_b$ group in which R$_a$ is selected from the group consisting of hydrogen and $C_{1-4}$ alkyl, and R$_b$ is selected from the group consisting of hydrogen, $C_{1-3}$ alkyl, and optionally substituted phenyl.

The term "$C_{1-7}$ amido" refers to a —NHC(O)R$_c$ group in which R$_c$ is selected from the group consisting of hydrogen, $C_{1-6}$ alkyl, and optionally substituted phenyl.

The term "$C_{1-5}$ carbamoyl" refers to an O- or N-linked carbamate substituted with a terminal $C_{1-4}$ alkyl.

The term "$C_{1-5}$ ureido" refers to a urea optionally substituted with a $C_{1-4}$ alkyl.

The term "$C_{1-8}$ alkylamino" refers to a —NR$_d$R$_e$ group in which R$_d$ is a $C_{1-4}$ alkyl and R$_e$ is selected from the group consisting of hydrogen and $C_{1-4}$ alkyl.

The term "$C_{6-10}$ aryl" refers to a monocyclic and polycyclic unsaturated, conjugated hydrocarbon having five to ten carbon atoms, and includes phenyl, and naphthyl.

More particularly "$C_{6-10}$ aryl" refers to phenyl.

The term "optionally substituted $C_{6-10}$ aryl" refers to a $C_{6-10}$ aryl optionally substituted with 1 to 5 substituents independently selected from the group consisting of optionally substituted $C_{1-4}$ alkyl, optionally substituted $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, cyano, halo, and hydroxyl.

More particularly "optionally substituted $C_{6-10}$ aryl" refers to a $C_{6-10}$ aryl optionally substituted with 1 to 5 substituents independently selected from the group consisting of $C_{1-4}$ alkyl, $C_{1-4}$ alkoxy, cyano, halo, hydroxy, amino, trifluoromethyl, and trifluoromethoxy.

Even more particularly "optionally substituted $C_{6-10}$ aryl" refers to phenyl optionally substituted with 1 to 5 substituents independently selected from the group consisting of $C_{1-4}$ alkyl, $C_{1-4}$ alkoxy, cyano, halo, trifluoromethyl, and trifluoromethoxy.

The term "$C_{1-5}$ oxycarbonyl" refers to an oxycarbonyl group (—$CO_2H$) and $C_{1-4}$ alkyl ester thereof.

The term "$C_{1-5}$ carbonyloxy" refers to a carbonyloxy group (—$O_2CR_f$), in which $R_f$ is selected from the group consisting of hydrogen and $C_{1-4}$ alkyl, for example, acetoxy.

The term "$C_{3-8}$ cycloalkyl" refers to monocyclic or bicyclic, saturated or partially (but not fully) unsaturated alkyl ring of three to eight carbon atoms, and includes cyclopropyl, cyclobutyl, cyclopentyl, cyclohexyl, and the like. It is understood that the term includes benzofused cyclopentyl and cyclohexyl.

The term "optionally substituted $C_{3-8}$ cycloalkyl" refers to a $C_{3-8}$ cycloalkyl optionally substituted with 1 to 6 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

More particularly "optionally substituted $C_{3-8}$ cycloalkyl" refers to a $C_{3-8}$ cycloalkyl optionally substituted with 1 to 3 substituents independently selected from the group consisting of $C_{1-4}$ alkoxy, halo, hydroxy, and $C_{1-4}$ alkyl optionally substituted with $C_{1-4}$ alkoxy, halo, and hydroxy.

The term "$C_{3-8}$ cycloalkoxy" refers to a $C_{3-8}$ cycloalkyl attached through and oxygen.

The terms "halogen" and "halo" refers to a chloro, fluoro, bromo or iodo atom.

The term "$C_{3-6}$ heterocyclyl" refers to a 4 to 8 membered monocyclic or bicyclic, saturated or partially (but not fully) unsaturated ring having one or two heteroatoms selected from the group consisting of nitrogen, oxygen, and sulfur and the ring optionally includes a carbonyl to form a lactam or lactone. It is understood that where sulfur is included that the sulfur may be either —S—, —SO—, and —$SO_2$—. It is also under that the term includes spirofused bicyclic systems. For example, but not limiting, the term includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl, and the like. It is understood that a $C_{3-6}$ heterocyclyl can be attached as a substituent through a ring carbon or a ring nitrogen atom.

More particularly "$C_{3-6}$ heterocyclyl" is selected from the group consisting of azetidinyl, pyrrolidinyl, piperidinyl, piperazinyl, morpholinyl, oxetanyl, tetrahydropyranyl, tetrahydrothiopyranyl, and tetrahydrofuryl.

The term "optionally substituted $C_{3-6}$ heterocyclyl" refers to a $C_{3-6}$ heterocyclyl optionally substituted on the ring carbons with 1 to 4 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally substituted on any ring nitrogen with a substituent independently selected from the group consisting of optionally substituted $C_{1-4}$ alkyl, $C_{3-8}$ cycloalkyl, optionally substituted $C_{3-6}$ heterocyclyl, optionally substituted $C_{1-10}$ heteroaryl, and optionally substituted phenyl.

More particularly "optionally substituted $C_{3-6}$ heterocyclyl" refers to a $C_{3-6}$ heterocyclyl optionally substituted on the ring carbons with 1 to 4 substituents independently selected from the group consisting of $C_{1-4}$ alkyl, $C_{1-4}$ alkoxy, halo, and hydroxy and optionally substituted on any ring nitrogen with a $C_{1-4}$ alkyl.

The term "$C_{1-10}$ heteroaryl" refers to a five to thirteen membered, monocyclic or polycyclic fully unsaturated, ring or ring system with one to ten carbon atoms and one or more, typically one to four, heteroatoms selected from the group consisting of nitrogen, oxygen, and sulfur. For example, but not limiting, the term includes furyl, thienyl, pyrrolyl, imidazolyl, isothiazolyl, isoxazolyl, oxadiazolyl, oxazolyl, thiazolyl, thiadiazolyl, triazolyl, tetrazolyl, pyrazinyl, pyrazolyl, pyridazinyl, pyridyl, pyrimidyl, azepinyl, diazepinyl, benzazepinyl, benzodiazepinyl, benzofuryl, benzothienyl, indolyl, isoindolyl, benzimidazolyl, benzisothiazolyl, benzisoxazolyl, benzoxadiazolyl, benzoxazolyl, benzopyrazinyl, benzopyrazolyl, imidazopyridyl, pyrazolopyridyl, pyrrolopyridyl, quinazolyl, thienopyridyl, imidazopyridyl, quinolyl, isoquinolyl benzothiazolyl, and the like. It is understood that a $C_{1-10}$ heteroaryl can be attached as a substituent through a ring carbon or a ring nitrogen atom where such an attachment mode is available, for example for a pyrrolyl, indolyl, imidazolyl, pyrazolyl, azepinyl, triazolyl, pyrazinyl, etc.

More particularly "$C_{1-10}$ heteroaryl" is selected from the group consisting of furyl, thienyl, pyrrolyl, imidazolyl, oxazolyl, thiazolyl, pyrazolyl, triazolyl, pyridyl, and pyrimidyl.

The term "optionally substituted $C_{1-10}$ heteroaryl" refers to a $C_{1-10}$ heteroaryl optionally substituted with 1 to 5 substituents on carbon independently selected from the group consisting of amino, $C_{1-8}$ alkylamino, $C_{1-9}$ amide, $C_{1-7}$ amido, $C_{1-5}$ carbamoyl, $C_{1-6}$ sulfonylamido, aminosulfonyl, $C_{1-10}$ aminosulfonyl, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ carbonyloxy, $C_{1-5}$ oxycarbonyl, and $C_{1-8}$ sulfonyl and optionally substituted with a substituent on each nitrogen independently selected from the group consisting of optionally substituted $C_{1-4}$ alkyl, $C_{1-8}$ sulfonyl, optionally substituted $C_{3-6}$ heterocyclyl, and optionally substituted phenyl.

More particularly "optionally substituted $C_{1-10}$ heteroaryl" refers to a $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxyl, oxo, trifluoromethyl, and trifluoromethoxy and optionally substituted on a ring nitrogen with a $C_{1-4}$ alkyl.

Even more particularly "optionally substituted $C_{1-10}$ heteroaryl" refers to a $C_{1-10}$ heteroaryl selected from the group consisting of furyl, thienyl, pyrrolyl, imidazolyl, oxazolyl, thiazolyl, pyrazolyl, diazolyl, pyridyl, pyrimidyl, and triazolyl each optionally substituted with 1 to 3 substituents independently selected from the group consisting of $C_{1-4}$ alkyl, $C_{1-4}$ alkoxy, cyano, halo, trifluoromethyl, and trifluoromethoxy and optionally substituted on a ring nitrogen with a methyl.

The term "oxo" refers to an oxygen atom doubly bonded to the carbon to which it is attached to form the carbonyl of a ketone or aldehyde. For example, a pyridone radical is contemplated as an oxo substituted $C_{1-10}$ heteroaryl.

The term "optionally substituted phenyl" refers to a phenyl group optionally substituted with 1 to 5 substituents independently selected from the group consisting of $C_{1-4}$ alkyl, $C_{1-4}$ alkoxy, $C_{1-6}$ amide, amino, $C_{1-8}$ alkylamino, $C_{1-5}$ oxycarbonyl, cyano, halo, hydroxyl, nitro, $C_{1-8}$ sulfonyl, and trifluoromethyl.

More particularly "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxyl, nitro, and trifluoromethyl.

The term "$C_{1-6}$ sulfonylamido" refers to a —NHS(O)$_2$—R$_g$ group wherein R$_g$ is selected from the group consisting of $C_{1-6}$ alkyl and optionally substituted phenyl.

The term "aminosulfonyl" refers to a —S(O)$_2$NH$_2$.

The term "$C_{1-10}$ aminosulfonyl" refers to a —S(O)$_2$NR$_h$R$_i$ group wherein R$_h$ is selected from the group consisting of hydrogen and $C_{1-4}$ alkyl and R$_i$ is selected from the group consisting of $C_{1-4}$ alkyl, and optionally substituted phenyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases or inorganic acids and bases. Such salts are well known in the art and include those described in Journal of Pharmaceutical Science, 66, 2-19 (1977). An example is the hydrochloride salt.

The term "substituted," including when used in "optionally substituted" refers to one or more hydrogen radicals of a group are replaced with non-hydrogen radicals (substituent(s)). It is understood that the substituents may be either the same or different at every substituted position. Combinations of groups and substituents envisioned by this invention are those that are stable or chemically feasible.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that, where the terms defined herein mention a number of carbon atoms, the mentioned number refers to the mentioned group and does not include any carbons that may be present in any optional substituent(s) thereon.

The skilled artisan will appreciate that certain of the compounds of the present invention exist as isomers. All stereoisomers of the compounds of the invention, including geometric isomers, enantiomers, and diastereomers, in any ratio, are contemplated to be within the scope of the present invention.

The skilled artisan will appreciate that certain of the compounds of the present invention exist as tautomers. All tautomeric forms the compounds of the invention are contemplated to be within the scope of the present invention.

Compounds of the invention also include all pharmaceutically acceptable isotopic variations, in which at least one atom is replaced by an atom having the same atomic number, but an atomic mass different from the predominant atomic mass. Isotopes suitable for inclusion in compounds of formula I include radioactive isotopes.

The terms "compounds of the invention" and "a compound of the invention" and "compounds of the present invention, and the like include the embodiment of formula I and the other more particular embodiments encompassed by formula I described herein and exemplified compounds described herein and a pharmaceutically acceptable salt of each of these embodiments.

(a) One embodiment relates to compounds of formula I wherein $X_1$ is CH and $X_2$ is N.

(b) One embodiment relates to compounds of formula I wherein $X_1$ is N and $X_2$ is N.

(c) One embodiment relates to compounds of formula I and embodiment (a) and (b) wherein $X_3$ is CCH$_3$ and $X_4$ is N.

(d) One embodiment relates to compounds of formula I and embodiment (a) and (b) wherein $X_3$ is N and $X_4$ is CCH$_3$.

(e) One embodiment relates to compounds of formula I and embodiments (a), (b), (c), and (d) wherein R$_1$ is optionally substituted $C_{6-10}$ aryl.

(f) One embodiment relates to compounds of formula I and embodiments (a), (b), (c), (d), and (e) wherein Z is $C_{1-6}$ alkylene.

(g) One embodiment relates to compounds formula I and embodiments (a), (b), (c), (d), and (e) wherein Z is $C_{1-6}$ haloalkylene.

(h) One embodiment relates to compounds formula I and embodiments (a), (c), (d), and (e) wherein Z is —O—.

(i) One embodiment relates to compounds of formula I and embodiments (a), (b), (c), (d), and (e) wherein Z is —C(O)—.

(j) One embodiment relates to compounds of formula I and embodiments (a), (b), (c), (d), (e), (f), (g), (h), and (i) wherein R$_2$—NR$_6$R$_7$. In another embodiment within embodiment (j), R$_6$ is hydrogen and R$_7$ is $C_{1-6}$ alkyl. In yet another embodiment within embodiment (j), R$_6$ is hydrogen and R$_7$ is $C_{3-8}$ cycloalkyl. In yet another embodiment within embodiment (j), R$_6$ is hydrogen and R$_7$ is $C_{3-6}$ heterocyclyl.

(k) One embodiment relates to compounds of formula I and embodiments (a), (b), (c), (d), (e), (f), (g), (h), (i), and (j) wherein s is 1.

(l) One embodiment relates to compounds of formula I and embodiments (a), (b), (c), (d), (e), (f), (g), (h), (i), (j), and (k) wherein q is 1.

(ay) Another embodiment relates to a pharmaceutically acceptable salt of each of the above embodiments.

(az) Another embodiment relates to a pharmaceutically acceptable salt of each of the exemplified compounds.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991). In the schemes below starting materials are either commercially available or can be ready prepared by methods well known in the art.

Scheme A

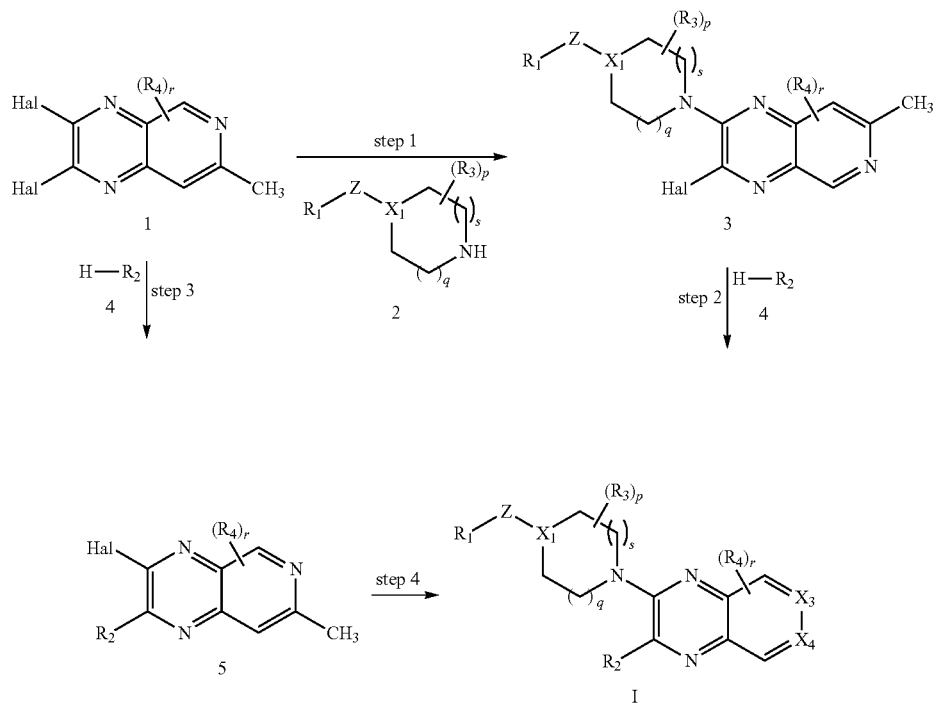

Scheme A depicts the formation of compounds in which $X_2$ is N.

In Scheme A, step 1, an appropriate compound of formula 1 is contacted with an appropriate compound of formula 2 to give a compound of formula 3. An appropriate compound of formula 1 is one in which Hal is a halogen and $R_4$ and r are as desired in the final compound of formula I. An appropriate compound of formula 2 is one in which $R_1$, Z, $R_3$, p, s, and q are as desired in the final compound of formula I or give rise to $R_1$, Z, and $R_3$ as desired in the final compound of formula I. Compounds of formula 2 are either commercially available or they can be readily prepared by methods well known in the art. For example, compounds of formula 2 where Z is oxygen can be prepared by Mitsunobu reaction between a piperidinol and an aryl alcohol.

The reaction is carried out in a suitable organic solvent like dioxane, n-butanol, dimethyl sulfoxide and the like with or without base such as diisopropylethylamine and triethylamine. The reaction is generally carried out at a temperature of from 0 to 80° C.

It is understood that a compound of formula 1 can also be treated with piperazine to give rise to compounds in which $X_1$ is N. The piperazine derivative can be further modified by reductive amination, alkylation, arylation, amidation, sulfonylation and the like to provide a compound of formula 3. Also the piperazine can be protected and elaborated as mentioned above after deprotection in a later step if desired.

In Scheme A, step 2, a compound of formula 3 is contacted with an appropriate compound of formula 4 to give a compound of formula I. An appropriate compound of formula 4 is $HOR_5$ or $HNR_6R_7$ in which $R_5$ or $R_6$ and $R_7$ are as desired in the final compound of formula I.

Where the compound of formula 4 is an amine, $HNR_6R_7$, the reaction is carried out in a suitable organic solvent like dioxane, ethanol, tetrahydrofuran, dimethyl sulfoxide, N,N-dimethylformamide and the like, with or without a base such as sodium hydroxide, diisopropylethylamine or triethylamine. The reaction is generally carried out at temperature between 20 to 150° C.

Where the compound of formula 4 is an alcohol, $HOR_5$, the reaction is carried out in a suitable organic solvent like dioxane, tetrahydrofuran, dimethyl sulfoxide, N,N-dimethylformamide and the like, with a base such as sodium hydride, lithium hydride, potassium t-butoxide, and the like. The reaction is generally carried out at temperature between 0 to 150° C.

Alternatively, as depicted in Scheme A, step 3, using the methodology described above, an appropriate compound of formula 1 can be contacted with an appropriate compound of formula 2 to give a compound of formula 5.

As depicted in Scheme A, step 4, a compound of formula 5 can be contacted with a compound of formula 2 to give a compound of formula I.

It will be recognized by one of ordinary skill in the art that the steps in Scheme A may be varied to provide compounds of formula I. In particular, the order of the steps required to produce the compounds of formula I is dependent upon the particular compound being synthesized, the starting compound, and the relative lability of the substituted moieties. Other variations are possible and are readily understood by the skilled person.

Scheme B

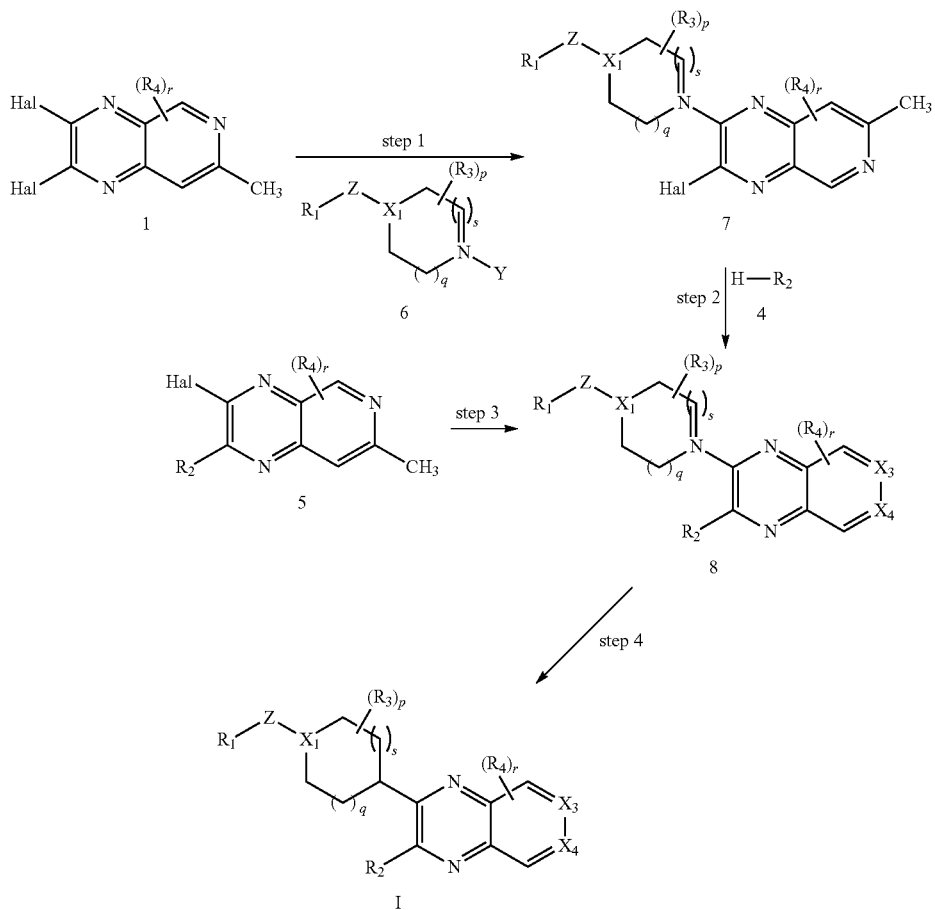

Scheme B depicts the formation of compounds in which $X_2$ is CH.

In Scheme B, step 1, an appropriate compound of formula 1, as described above, is contacted with an appropriate compound of formula 6 to give a compound of formula 7. An appropriate compound of formula 6 is one in which $R_1$, Z, $R_3$, p, s, and q are as desired in the final compound of formula I or give rise to $R_1$, Z, and $R_3$ as desired in the final compound of formula I and Y a boronic acid or boronic ester. It is also understood that the group depicted as $R_1$—Z— can be replaced by an appropriate protecting group, such a methyl, benzyl, t-BOC, or Cbz, subsequent removal of the protecting group and installation of $R_1$—Z— as desired in the final product of formula I.

Such reactions are generally known as a Suzuki reaction and are well known in the art. While a Suzuki reaction is depicted in Scheme B it is understood that other carbon-carbon bond forming coupling reactions can be used with compounds of formula 6 having Y other than boronic acid or esters to produce compounds of formula I.

In Scheme B, step 2, a compound of formula 7 is contacted with an appropriate compound of formula 4 to give a compound of formula 8. An appropriate compound of formula 4 and general reaction conditions are described above in Scheme A, step 2.

Alternately, Scheme B, step 3, depicts Suzuki reaction with an appropriate compound of formula 6 and an appropriate compound of formula 5 as described above to give a compound of formula 8.

In Scheme B, step 4, a compound of formula 8 is reduced to a compound of formula I. Such reductions are well known in the art. The reaction is carried out in a suitable organic solvent like dioxane, ethanol, methanol, isopropanol, tetrahydrofuran, and the like. The reaction is generally carried out using hydrogen and a catalyst, such as platinum or palladium catalyst.

It will be recognized by one of ordinary skill in the art that the steps in Scheme B may be varied to provide compounds of formula I. In particular, the order of the steps required to produce the compounds of formula I is dependent upon the particular compound being synthesized, the starting compound, and the relative lability of the substituted moieties.

It is also understood that some compounds of formula I may be elaborated to other compounds of formula I, in an additional steps not shown. Compounds of formula I may be elaborated in a variety of ways. Such reactions include hydrolysis, oxidation, reduction, alkylation, amidations, and the like. Also, in an optional step, not shown in the schemes above, the compounds of formula I can be converted to pharmaceutically acceptable salts by methods well known and appreciated in the art.

The following examples are intended to be illustrative and non-limiting, and represent specific embodiments of the present invention.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). Other abbreviations have their usual meaning unless otherwise indicated. The mass spectra, unless otherwise indicated, were recorded using either electrospray ionization (ESI) or atmospheric pressure chemical ionization.

The examples below were carried out in appropriate vessels and were typically stirred. Where indicated, products of certain preparations and examples are purified by HPLC. Where indicated products of the preparations and examples were purified by HPLC.

HPLC Method A: Pump: Shimadzu LC-8A; UV/Vis: SPD-20A; Software: LCSolution. A Phenomenex Gemini® C18, 5 µm, ID 30×100 mm column was used and eluted with gradients of ACN (containing 0.035% TFA) and water (containing 0.005% TFA). A 10% to 100% ACN gradient was used unless otherwise indicated.

HPLC Method B: Pump: Waters 2525 or 2545; MS: ZQ; Software: MassLynx. A Xbridge™ C18, 5 µm, ID 30×75 mm column was used and eluted with gradients of 10 mMol NH4HCO3 in water/acetonitrile (pH=9.5-10).

After isolation by chromatography, the solvent is removed and the product is obtained by evaporating product containing fractions (e.g., GeneVac™), rotary evaporator, evacuated flask, lyophilization, etc.

The abbreviations used throughout have their conventional meanings unless indicated otherwise. For example, the following abbreviations are used: ACN (acetonitrile); aq (aqueous); Boc or t-BOC (tert-butoxycarbonyl); Cbz (carbobenzyloxy); DCM (dichloromethane); DMSO (dimethyl sulfoxide); TFA (trifluoroacetic acid); HOAc (acetic acid), MeOH (methanol), PE (petroleum ether), EA or EtOAc (ethyl acetate) and the like.

Preparation 1
(5-chloro-2-fluorophenyl)(piperidin-4-yl)methanone

A solution of 2-bromo-4-chloro-1-fluorobenzene (175 µL, 1.377 mmol) in THF (4.59 mL) at 78° C. was treated with n-BuLi (2.6 M, 741 µL, 1.928 mmol) and the reaction mixture was stirred for 30 min. To this was added tert-butyl 4-(methoxy(methyl)carbamoyl)piperidine-1-carboxylate (250 mg, 0.918 mmol) in one portion. The cooling bath was removed and the resulting reaction mixture was allowed to warm to rt and stirred for 1.5 h. Purification by automated flash silica gel chromatography using 10% EtOAc in hexanes afforded tert-butyl 4-(5-chloro-2-fluorobenzoyl)piperidine-1-carboxylate (287.9 mg, 92%) as a yellow oil. ESI-MS m/z [M+Na]+ 364.20.

A solution of tert-butyl 4-(5-chloro-2-fluorobenzoyl)piperidine-1-carboxylate (287.9 mg, 0.843 mmol) in dioxane (2.41 mL) was treated with HCl (2.11 mL, 8.43 mmol) at rt and the resulting reaction mixture was stirred overnight. The reaction mixture was diluted with hexanes and filtered by suction to afford (5-chloro-2-fluorophenyl)(piperidin-4-yl)methanone as its HCl salt (146 mg, 62.3%) as a yellow solid. ESI-MS m/z [M+H]+ 242.20.

Preparation 2 4-(2,4-difluorophenoxy)piperidine

To a solution of 2,4-difluorophenol (10 g, 77 mmol), PPh3 (30.2 g, 115 mmol) and tert-butyl 4-hydroxypiperidine-1-carboxylate (30.9 g, 154 mmol) in THF (400 mL) was added DEAD (18.3 mL, 115 mmol) at 0° C. dropwise. After the addition was completed, the resulting mixture was allowed to stir at 40° C. for 16 h. The mixture was poured into water and extracted with EtOAc (3×400 mL). The combined organic layers were dried over Na2SO4, filtered and concentrated to give the crude product. Purification by flash silica gel chromatography, eluting with 80:1 PE: EtOAc, gave tert-butyl 4-(2,4-difluorophenoxy)piperidine-1-carboxylate as an oil (20 g, 83%).

A solution of tert-butyl 4-(2,4-difluorophenoxy)piperidine-1-carboxylate (20 g, 63.8 mmol) in 4:1 HCl/EtOAc (250 mL) was stirred at 25° C. for 1 h. The mixture was concentrated to give the title compound, as its HCl salt, as a white solid (15.4 g, 97%). 1H NMR (400 MHz, DMSO-d6) δ ppm 1.84 (m, 2H), 2.08 (m, 2H), 3.05 (m, 2H), 3.20 (m, 2H), 4.57 (m, 1H), 7.04 (m, 1H), 7.31 (m, 2H), 8.95 (br d, 2H).

Preparation 3
3-fluoro-4-(piperidin-4-yloxy)benzonitrile

A solution of 3,4-difluorobenzonitrile (28 g, 201 mmol) and tert-butyl 4-hydroxypiperidine-1-carboxylate (40.5 g, 201 mmol) in THF (500 mL) was treated with sodium hydride (4 g, 100 mmoL) and stirred at 25° C. for 16 h. The reaction mixture was washed with water, extracted with EtOAc, and the crude product purified by flash silica gel chromatography gave tert-butyl 4-(4-cyano-2-fluorophenoxy)piperidine-1-carboxylate (25 g, 39%).

A solution of tert-butyl 4-(4-cyano-2-fluorophenoxy)piperidine-1-carboxylate (42 g, 131 mmol) dissolved in 4:1 HCl/EtOAc (100 mL) was stirred for 5 h. The mixture was concentrated to give the title compound as its HCl salt (12 g, 36%). 1H NMR (400 MHz, DMSO-d6) δ ppm 1.89 (m, 2H), 2.14 (m, 2H); 3.08 (m, 2H), 3.21 (m, 2H), 4.86 (m, 1H), 7.48 (t, J=8.4 Hz, 1H), 7.70 (d, J=8.4 Hz, 1H), 7.89 (m, 1H); ESI-MS m/z [M+H]+ 220.7.

Preparation 4
4-((2,4-difluorophenyl)fluoromethyl)piperidine

To a 0° C. solution of tert-butyl 4-(2,4-difluorobenzoyl)piperidine-1-carboxylate (1.28 g, 3.93 mmol) in MeOH (15.7 mL) was added NaBH4 (0.372 g, 9.84 mmol). The ice bath was removed and the reaction mixture stirred for 2 h at room temperature then was quenched with saturated aqueous NH4Cl. The organic layer was extracted with EtOAc, washed with water and dried over MgSO4. The solvent was removed under reduced pressure gave tert-butyl 4-((2,4-difluorophenyl)(hydroxy)methyl)piperidine-1-carboxylate as a white hygroscopic solid.

To a 78° C. solution of tert-butyl 4-((2,4-difluorophenyl)(hydroxy)methyl)piperidine-1-carboxylate (200 mg, 0.611 mmol) in DCM (3.055 mL) was added DAST (242 µL, 1.833 mmol). The mixture was stirred at 78° C. for 30 min, then quenched with MeOH. Flash silica gel chromatography using a gradient of 0% to 100% EtOAc in hexanes gave tert-butyl 4-((2,4-difluorophenyl)fluoromethyl)piperidine-1-carboxylate as a colorless oil.

To a solution of racemic tert-butyl 4-((2,4-difluorophenyl)fluoromethyl)piperidine-1-carboxylate (148 mg, 0.449 mmol) in dioxane (1.50 mL) was added HCl (4 M in dioxane, 337 µL, 1.348 mmol). The mixture was heated at 45° C. for 16 h then concentrated in vacuo to give the title compound as its HCl salt (109 mg, 91%) as a white solid.

Preparation 5
(R)-4-((2,4-difluorophenyl)fluoromethyl)piperidine tert-Butyl 4-((2,4-difluorophenyl)fluoromethyl)piperidine-1-carboxylate was subjected to chiral SFC separation to give (R)-tert-butyl 4-((2,4-difluorophenyl)fluoromethyl)piperidine-1-carboxylate. (R)-tert-butyl 4-((2,4-difluorophenyl)fluoromethyl)piperidine-1-carboxylate (2.8 g, 8.50 mmol) was dissolved in EtOAc (20 mL) and HCl (4 M in EtOAc, 21 mL) was added. The reaction mixture was stirred at 23° C. for 2 h. Evaporation of the solvent gave the title compound as its HCl salt (2.1 g, 93%). ESI-MS m/z [M+H]+ 229.9.

Preparation 6
(S)-4-((2,4-difluorophenyl)fluoromethyl)piperidine tert-Butyl 4-((2,4-difluorophenyl)fluoromethyl)piperidine-1-carboxylate as was subjected to chiral SFC separation to give (R)-tert-butyl 4-((2,4-difluorophenyl)fluoromethyl)piperidine-1-carboxylate. The HCl salt of the title compound was prepared in similar fashion to Preparation 5, using (S)-tert-butyl 4-((2,4-difluorophenyl)fluoromethyl)piperidine-1-carboxylate. ESI-MS m/z [M+H]+ 229.9.

Preparation 7 4-((2-fluorophenyl)sulfonyl)piperidine

A mixture of 2-fluorobenzenethiol (0.764 mL, 7.15 mmol), tert-butyl 4-((methylsulfonyl)oxy)piperidine-1-carboxylate (1.816 g, 6.5 mmol), and K2CO3 (1.348 g, 9.75 mmol) in ACN (16.25 mL) was heated at 80° C. overnight. The reaction mixture was poured into water and extracted twice with EtOAc. The combined organics were dried over sodium sulfate, filtered, and concentrated under reduced pressure gave tert-butyl 4-((2-fluorophenyl)thio)piperidine-1-carboxylate as a yellow oil (1.98 g, 98%), which was carried forward without purification.

A solution of tert-butyl 4-((2-fluorophenyl)thio)piperidine-1-carboxylate (1.98 g, 6.36 mmol) in THF (54.5 mL) and MeOH (18.2 mL) at 0° C. was treated with a cold solution of Oxone® (9.77 g, 15.9 mmol) in water (54.5 mL). The reaction mixture was stirred for 5 h, gradually warming to room temperature. The reaction mixture was poured into water and extracted twice with EtOAc. The combined organics were washed with water and then saturated aqueous NaCl, dried over Na2SO4, filtered, and concentrated under reduced pressure. The residue was purified by flash silica gel chromatography using a gradient of 10% to 50% EtOAc with 0.1% triethylamine in heptanes gave tert-butyl 4-((2-fluorophenyl)sulfonyl)piperidine-1-carboxylate as a pale yellow oil (1.31 g, 60%).

A solution of tert-butyl 4-((2-fluorophenyl)sulfonyl)piperidine-1-carboxylate (1.31 g, 3.82 mmol) in dioxane (12.7 mL) at room temperature was treated with 4M HCl in dioxane (9.55 ml, 38.2 mmol). The reaction mixture was allowed to stir at room temperature overnight. The reaction mixture was concentrated under reduced pressure. The resulting white solid was triturated with hexanes, filtered, collected, and lyophilized overnight to give the title compound, as its HCl salt, as a white solid (815.1 mg, 76%). ESI-MS m/z [M+H]+ 243.95.

Preparation 8
4-((2-fluoro-4-methoxyphenyl)sulfonyl)piperidine

A mixture of 2,4-difluorobenzenethiol (0.810 mL, 7.15 mmol), tert-butyl 4-((methylsulfonyl)oxy)piperidine-1-carboxylate (1.816 g, 6.5 mmol), and K2CO3 (1.348 g, 9.75 mmol) in ACN (16.25 mL) was heated at 80° C. overnight. The reaction mixture was poured into water and extracted twice with EtOAc. The organic layer was dried over Na2SO4, filtered, and concentrated under reduced pressure to afford tert-butyl 4-((2,4-difluorophenyl)thio)piperidine-1-carboxylate (2.141 g) as a yellow oil, which was carried forward without purification.

A solution of tert-butyl 4-((2,4-difluorophenyl)thio)piperidine-1-carboxylate (2.141 g, 6.50 mmol) in THF/MeOH (3:1, 74 mL) at 0° C. was treated with a cold solution of Oxone® (9.99 g, 16.25 mmol) in water (56 mL). The reaction mixture was allowed to stir overnight, gradually warming to room temperature. The reaction mixture was poured into water and extracted twice with EtOAc. The combined organics were washed with water and then saturated aqueous NaCl, dried over Na2SO4, filtered, and concentrated under reduced pressure. The residue was purified by flash silica gel chromatography using a gradient of 10% to 40% EtOAc with 0.1% triethylamine in heptanes gave tert-butyl 4-((2,4-difluorophenyl)sulfonyl)piperidine-1-carboxylate (1.32 g, 56%) as a white solid. ESI-MS m/z [M+Na]+ 383.80.

To a suspension of tert-butyl 4-((2,4-difluorophenyl)sulfonyl)piperidine-1-carboxylate (50 mg, 0.138 mmol) in MeOH (461 µl) was added sodium methoxide (25.6 µL, 0.138 mmol, 5.4 M in MeOH) dropwise. The reaction mixture was allowed to stir at 45° C. for 20 min then concentrated in vacuo. Boc deprotection was carried out by addition of HCl (138 µL, 0.553 mmol, 4 M in dioxane) to the crude reaction mixture in 300 µL dioxane. Stirring at 50° C. for 24 h followed by concentration in vacuo yielded the title compound as its HCl salt (57 mg) as a white solid (10:1 regioisomeric mixture). ESI-MS m/z [M+H]+ 274.00.

Preparation 9 4-((3-fluorophenyl)sulfonyl)piperidine

A mixture of tert-butyl 4-((methylsulfonyl)oxy)piperidine-1-carboxylate (1.0 g, 3.58 mmol), K2CO3 (0.742 g, 5.37 mmol), and 3-fluorobenzenethiol (0.363 mL, 4.30 mmol) in ACN (7.5 mL) was stirred at 23° C. for 5 min. The reaction mixture was stirred at 80° C. for 17 h, cooled to 23° C. and partitioned between EtOAc and water. The layers were separated, the organic phase was washed with brine, dried over Na2SO4, filtered, rinsed with EtOAc, and dried in vacuo gave tert-butyl 4-((3-fluorophenyl)thio)piperidine-1-carboxylate (1.115 g, 100%) as a yellow oil. ESI-MS m/z [M+H]+ 255.9.

A mixture of basic alumina (3.0 g, 29.4 mmol) in water (0.6 mL) was stirred at 23° C. for 5 min. Next, ACN (12 mL) was added followed by a solution of tert-butyl 4-((3-fluorophenyl)thio)piperidine-1-carboxylate (1.115 g, 3.58 mmol) in CHCl3 (8 mL). Next, Oxone® (6.60 g, 10.74 mmol) was added and the reaction mixture was stirred at 60° C. for 19 h. The reaction mixture was cooled to 23° C., filtered, rinsed with CHCl3, and the filtrate was washed with water (10 mL). The organic layer was dried over Na2SO4, filtered, rinsed with CHCl3, and dried in vacuo. The crude residue was dissolved in toluene (5 mL) and purified via medium pressure chromatography using a gradient of 10% to 100% EtOAc with 0.1% triethylamine in heptane on a 80 g silica gel column (Single Step™) gave tert-butyl 4-((3-fluorophenyl)sulfonyl)piperidine-1-carboxylate (0.769 g, 62.5%) as a white solid. ESI-MS m/z [M+Na]+ 365.9.

To a solution of tert-butyl 4-((3-fluorophenyl)sulfonyl)piperidine-1-carboxylate (756 mg, 2.201 mmol) in dioxane (5.0 mL) was added HCl (4 M in dioxane, 5.50 mL, 22.01 mmol) at 23° C. The reaction was stirred at 23° C. for 21 h to furnish a white suspension. The resulting solid was filtered, rinsed with dioxane and dried in vacuo to give the title compound as its HCl salt (582.6 mg, 95%) as a white solid. ESI-MS m/z [M+H]+ 243.9.

Preparation 10
4-((3-methoxyphenyl)sulfonyl)piperidine

The title compound as its HCl salt was prepared in a similar manner to Preparation 9, with the exception that additional chloroform was used in place of ACN in the second step. ESI-MS m/z [M+H]+ 255.9.

Preparation 11
4-((4-fluorophenyl)sulfonyl)piperidine

A mixture of tert-butyl 4-((methylsulfonyl)oxy)piperidine-1-carboxylate (1.42 g, 5.08 mmol), 4-fluorobenzenethiol (0.663 ml, 6.10 mmol) and K2CO3 (1.054 g, 7.62 mmol) in ACN (12.71 mL) was stirred at 85° C. overnight. The reaction mixture was filtered by suction and the solvent removed gave tert-butyl 4-((4-fluorophenyl)thio)piperidine-1-carboxylate (1.5 g, 95%) as a white solid.

A solution of tert-butyl 4-((4-fluorophenyl)thio)piperidine-1-carboxylate (1.5 g) in water (16.06 mL) and MeOH (16.06 mL) was treated with Oxone® (5.92 g, 9.63 mmol) at room temperature and the resulting reaction mixture was stirred for 6 h. The solution was filtered by suction and the solvent removed gave tert-butyl 4-((4-fluorophenyl)sulfonyl)piperidine-1-carboxylate (1.6 g, 4.66 mmol, 97% yield) as a white solid.

A solution of tert-butyl 4-((4-fluorophenyl)sulfonyl)piperidine-1-carboxylate (32.7 mg, 0.095 mmol) in dioxane (238 µl) at room temperature was treated with HCl (4 M in dioxane, 190 µl, 0.762 mmol) and the resulting reaction mixture was stirred for 4 h. The solvent was removed to give the title compound as its HCl salt (25 mg, 94%) as a white solid. ESI-MS m/z [M+H]+ 243.95.

Preparation 12 1-(2,4-difluorobenzyl)piperazine

A mixture of piperazine (26.5 g, 308 mmol) in THF (350 mL) was heated to 70° C. and 1-(chloromethyl)-2,4-difluorobenzene (5 g, 30.8 mmol) was added. The suspension was heated at 70° C. overnight. The solid (piperazine) was filtered off, and the solvent was removed under reduced pressure. The residue was partitioned between EtOAc and water. The organic layer was dried and concentrated to give the title compound (6 g, 92%). ESI-MS m/z [M+H]+ 213.04.

Preparation 13
4-(2-fluoro-4-methoxyphenoxy)piperidine

A solution of tert-butyl 4-hydroxypiperidine-1-carboxylate (2.496 g, 12.03 mmol) in THF (33.4 mL) at room temperature was treated with 2-fluoro-4-methoxyphenol (1.181 mL, 10.03 mmol) and triphenylphosphine (3.16 g, 12.03 mmol). The reaction mixture was cooled to 0° C. and DEAD (40 wt % in toluene, 5.95 mL, 15.04 mmol) was added dropwise via syringe. The resulting reaction mixture was stirred at 65° C. for 5 h, then at room temperature overnight. Flash silica gel chromatography using a gradient of 10% to 100% EtOAc in hexanes gave tert-butyl 4-(2-fluoro-4-methoxyphenoxy)piperidine-1-carboxylate (2.78 g, 85%) as a light yellow oil. ESI-MS m/z [M+Na]+ 348.2.

A solution of tert-butyl 4-(2-fluoro-4-methoxyphenoxy)piperidine-1-carboxylate (2.78 g, 8.54 mmol) in dioxane (21.36 mL) was treated with HCl (4 M in dioxane, 21.36 mL, 85 mmol) at room temperature and the resulting reaction mixture stirred overnight. Flash silica gel chromatography using a gradient of 5% to 30% MeOH in DCM gave the title compound as its HCl salt (1.7 g, 76%) as a white solid. ESI-MS m/z [M+H]+ 226.20.

Preparation 14
1-(2-fluoro-4-methoxybenzyl)piperazine

A solution of 2-fluoro-4-methoxybenzaldehyde (0.910 g, 5.91 mmol) and tert-butyl piperazine-1-carboxylate (1.1 g, 5.91 mmol) in DCE (19.7 ml) was treated with sodium triacetoxyborohydride (1.752 g, 8.27 mmol) and the resulting reaction mixture was stirred at 23° C. for 2 h. The crude material was purified by a flash chromatography column using a gradient of 0-50% EtOAc in heptane to give tert-butyl 4-(2-fluoro-4-methoxybenzyl)piperazine-1-carboxylate (1.91 g, 100% yield) as a clear oil.

A solution of tert-butyl 4-(2-fluoro-4-methoxybenzyl)piperazine-1-carboxylate (700 mg, 2.16 mmol) in DCM (10.8 mL) and TFA (10.8 mL) was stirred at 0° C. for 1 h. After the solvent was removed, HPLC purification using Method A gave the title compound as its TFA salt (250 mg, 34.2% yield) as a white solid. ESI-MS: m/z (M+H)+ 225.1.

Preparation 15
1-(4-(difluoromethoxy)-2-fluorobenzyl)piperazine

Combined 4-(difluoromethoxy)-2-fluorobenzaldehyde (0.5 g, 2.63 mmol), tert-butyl piperazine-1-carboxylate (0.490 g, 2.63 mmol) in DCE (10 mL) and then added sodium triacetoxyhydroborate (0.780 g, 3.68 mmol) at 23° C. The reaction mixture was stirred for 18 hr at 23° C., filtered through Celite™, and rinsed with DCM. The resulting filtrate was concentrated, and the residue was purified by flash silica gel chromatography (0-10% MeOH in DCM) to give tert-butyl 4-(4-(difluoromethoxy)-2-fluorobenzyl)piperazine-1-carboxylate (594.5 mg, 62.7% yield) as a colorless oil. 1H NMR (400 MHz, CDCl3-d) δ ppm 1.41-1.49 (m, 9H), 2.41 (br. s., 4H), 3.36-3.49 (m, 4H), 3.56 (s, 2H), 6.34-6.66 (m, 1H), 6.85 (dd, J=10.3, 2.4 Hz, 1H), 6.90 (dd, J=8.5, 2.2 Hz, 1H), 7.33-7.48 (m, 1H); ESI-MS: m/z (M+H)+ 361.5.

Combined tert-butyl 4-(4-(difluoromethoxy)-2-fluorobenzyl)piperazine-1-carboxylate (570 mg, 1.58 mmol) and hydrogen chloride as a 4 M solution in dioxane (3163 µl, 12.65 mmol) at 23° C. The reaction mixture was stirred at 23° C. for 3 hr. The precipitate was filtered, rinsed with dioxane (3×3 mL) and dried in vacuo to provide title compound as its hydrochloric acid salt (0.469 g, 100% yield) as a white solid. 1H NMR (400 MHz, DMSO-d6) δ ppm 2.78-3.56 (m, 8H), 4.29 (br, 2H), 7.15 (d, J=7.8 Hz, 1H), 7.21-7.59 (m, 2H), 7.76 (br, 1H), 9.46 (br, 2H); ESI-MS: m/z (M+H)+ 261.0.

Preparation 16
4-(4-(difluoromethoxy)-2-fluorophenoxy)piperidine

Tribromoborane (34.4 ml, 34.4 mmol) was added to a suspension of 4-(2-fluoro-4-methoxyphenoxy)piperidine hydrochloride (3.0 g, 11.46 mmol) in DCM (22.9 ml) at 0° C. After 10 min, the mixture was allowed to warm to 23° C. for 3 h. The reaction mixture was quenched with water dropwise at 0° C. until no more bubble formed upon addition, then was allowed to warm to 23° C. Additional water (100 mL) was added to the mixture and the suspension was stirred at rt for 1 h. Then the mixture was filtered through a pad of Celite, washed with water. The layers were separated and the aqueous phase was washed with DCM twice. The aqueous phase was concentrated under reduced pressure to give 3-fluoro-4-(piperidin-4-yloxy)phenol (3.35 g, 11.47 mmol, 100% yield) as a light-orange solid, which was used without further purification.

A solution of 3-fluoro-4-(piperidin-4-yloxy)phenol hydrobromide (16.59 g, 56.8 mmol) in water (175 mL) and dioxane (100 ml) was basified with NaOH (15%) to pH=9 at 0° C., followed by addition of Boc2O (19.78 ml, 85 mmol). The mixture was allowed to warm to 25° C. for 12 h. The mixture was acidified with acetic acid to pH=7, diluted with EtOAc (100 ml) and poured into sat. NaHCO3 (50 mL). The organic layer was separated, washed with brine (2×30 ml), dried over Na2SO4 and concentrated in vacuo. The residue was purified by column chromatography using a gradient of 20-90% EtOAc in petroleum ether to give tert-butyl 4-(2-fluoro-4-hydroxyphenoxy)piperidine-1-carboxylate (9.2 g, 52.0% yield) as a yellow solid. ESI-MS: m/z (M-CMe3)+ 255.7.

To a mixture of tert-butyl 4-(2-fluoro-4-hydroxyphenoxy) piperidine-1-carboxylate (126 mg, 0.41 mmol) and Cs2CO3 (198 mg, 0.61 mmol) in DMF (4.0 mL) was added a solution of difluoroiodomethane (1440 mg, 0.81 mmol, 10 wt %) in THF. The reaction mixture was stirred at 23° C. overnight. After the solvent was evaporated in vacuo, the residue was purified by flash silica gel chromatography (5-95% EA in heptane) to give tert-butyl 4-(4-(difluoromethoxy)-2-fluorophenoxy)piperidine-1-carboxylate (18 mg, 12.3% yield) as a white solid. (M+H)+ 362.0.

A solution of tert-butyl 4-(4-(difluoromethoxy)-2-fluorophenoxy)piperidine-1-carboxylate (18 mg, 0.05 mmol) in DCM (0.5 ml) and TFA (0.5 ml) was stirred at 0° C. for 2 h. Removal of the solvent gave the title compound as its TFA salt (18 mg, 0.05 mmol, 96% yield) as a white solid, which was used directly in the next step without further purification. (M+H)+ 262.0.

Preparation 17 3-chloro-N-isopropyl-7-methyl-pyrido[3,4-b]pyrazin-2-amine

To a solution of 2,3-dichloro-7-methylpyrido[3,4-b]pyrazine (100 mg, 0.47 mmol) in DCM (4.6 mL) was added propan-2-amine (80 µl, 0.93 mmol) and N-ethyl-N-isopropylpropan-2-amine (245 µl, 1.40 mmol) at 0° C. The resulting solution was stirred at 0° C. for 4 h, warmed to 23° C. and stirred overnight. The solvent was removed in vacuo, and the crude material was dissolved in DCM (4 mL) and purified via flash column chromatography using a gradient eluant of 0% to 100% EtOAc in heptane on a 24 g. The pure fractions were concentrated, and dried in vacuo to give the title compound (79 mg, 0.33 mmol, 71.4% yield) as a grey solid. ESI-MS m/z [M+H]+ 237.0.

Preparation 18 (S)-3-chloro-7-methyl-N-(tetrahydrofuran-3-yl)pyrido[3,4-b]pyrazin-2-amine The title compound was prepared in a manner similar to the Preparation 17 using (S)-tetrahydrofuran-3-amine tosylic acid salt in place of propan-2-amine. ESI-MS m/z [M+H]+ 265.0.

Preparation 19 (R)-3-chloro-7-methyl-N-(tetrahydrofuran-3-yl)pyrido[3,4-b]pyrazin-2-amine The title compound was prepared in a manner similar to the Preparation 17 using (R)-tetrahydrofuran-3-amine hydrochloric acid salt in place of propan-2-amine, to give the title compound (41%) as a white solid. ESI-MS m/z [M+H]+ 264.9.

Preparation 20 3-chloro-7-methyl-N-(tetrahydrofuran-3-yl)pyrido[3,4-b]pyrazin-2-amine The title compound was prepared in a manner similar to the Preparation 17 using tetrahydrofuran-3-amine hydrochloric acid salt in place of propan-2-amine. ESI-MS m/z [M+H]+ 265.0.

Preparation 21 3-chloro-N-cyclopropyl-7-methyl-pyrido[3,4-b]pyrazin-2-amine

The title compound was prepared in a manner similar to the Preparation 17 using cyclopropanamine in place of propan-2-amine. ESI-MS m/z [M+H]+ 235.0.

Preparation 22 (1,3-cis)-3-((3-chloro-7-methyl-pyrido[3,4-b]pyrazin-2-yl)amino)cyclobutanol The title compound was prepared in a manner similar to the Preparation 17 using (1,3-cis)-3-aminocyclobutanol in place of propan-2-amine. ESI-MS m/z [M+H]+ 265.0.

Preparation 23 (1,3-trans)-3-((3-chloro-7-methyl-pyrido[3,4-b]pyrazin-2-yl)amino)cyclobutanol The title compound was prepared in a manner similar to the Preparation 17 using (1,3-trans)-3-aminocyclobutanol in place of propan-2-amine. ESI-MS m/z [M+H]+ 265.0.

Preparation 24 3-chloro-7-methyl-N-(oxetan-3-yl)pyrido[3,4-b]pyrazin-2-amine

The title compound was prepared in a manner similar to the Preparation 17 using oxetan-3-amine in place of propan-2-amine. ESI-MS m/z [M+H]+ 250.9.

Preparation 25 3-chloro-2-(4-(2-fluoro-4-methoxybenzyl)piperazin-1-yl)-7-methylpyrido[3,4-b]pyrazine A solution of 2,3-dichloropyrido[3,4-b]pyrazine (125.0 mg, 0.584 mmol) in DCM (4.0 mL) at 0° C. was treated with 1-(2-fluoro-4-methoxybenzyl)piperazine (206.0 mg, 0.642 mmol) and DIPEA (0.306 mL, 1.752 mmol). The reaction mixture was allowed to stir for 3 h at 0° C. and then at room temperature for 1 h.

After the solvent was removed in vacuo, the crude material was dissolved in DCM (4 mL) and purified via flash silica gel chromatography using a gradient eluant of 10% to 70% EtOAc in heptane. The pure fractions were combined, concentrated via rotary evaporation, and dried in vacuo to furnish the title compound (97 mg, 41%). ESI-MS m/z [M+H]+ 402.5.

Preparation 26 3-chloro-2-(4-(4-(difluoromethoxy)-2-fluorophenoxy)piperidin-1-yl)-7-methylpyrido[3,4-b]pyrazine The title compound was prepared in a manner similar to the Preparation 25 using 4-(4-(difluoromethoxy)-2-fluorophenoxy)piperidine hydrochloride in place of 1-(2-fluoro-4-methoxybenzyl)piperazine. ESI-MS m/z [M+H]+ 439.3.

Preparation 27 3-chloro-2-(4-(2,4-difluorophenoxy)piperidin-1-yl)-7-methylpyrido[3,4-b]pyrazine The title compound was prepared in a manner similar to the Preparation 25 using 4-(2,4-difluorophenoxy)piperidine hydrochloride in place of 1-(2-fluoro-4-methoxybenzyl)piperazine. ESI-MS m/z [M+H]+ 390.9.

Preparation 28 3-chloro-2-(4-(2,4-difluorobenzyl)piperazin-1-yl)-7-methylpyrido[3,4-b]pyrazine The title compound was prepared in a manner similar to the Preparation 25 using 1-(2,4-difluorobenzyl)piperazine hydrochloride in place of 1-(2-fluoro-4-methoxybenzyl)piperazine. ESI-MS m/z [M+H]+ 389.9.

Preparation 29 3-chloro-2-(4-(4-(difluoromethoxy)-2-fluorobenzyl)piperazin-1-yl)-7-methylpyrido[3,4-b]pyrazine The title compound was prepared in a manner similar to the Preparation 25 using 1-(4-(difluoromethoxy)-2-fluorobenzyl)piperazine hydrochloride in place of 1-(2-fluoro-4-methoxybenzyl)piperazine. 1H NMR (400 MHz, DMSO-d6) δ ppm 2.57-2.63 (m, 7H), 3.60 (s, 2H), 3.62-3.66 (m, 4H), 7.05 (dd, J=8.3, 2.4 Hz, 1H), 7.13 (dd, J=10.7, 2.4 Hz, 1H), 7.15-7.45 (m, 1H), 7.48-7.54 (m, 2H), 9.02 (s, 1H); ESI-MS m/z (M+H)+ 437.9.

Example 1 3-(4-(2,4-difluorobenzyl)piperazin-1-yl)-N-isopropyl-7-methylpyrido[3,4-b]pyrazin-2-amine

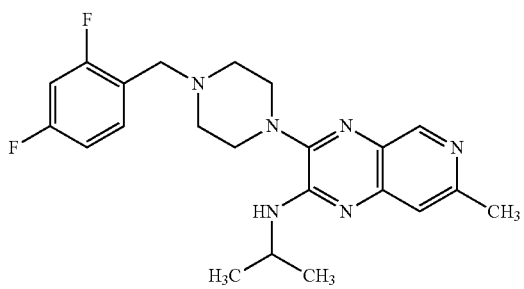 [SMILES: Cc1cc2nc(NC(C)C)c(N3CCN(Cc4ccc(F)cc4F)CC3)nc2cn1]

A solution of 3-chloro-N-isopropyl-7-methylpyrido[3,4-b]pyrazin-2-amine (20 mg, 0.084 mmol), 1-(2,4-difluorobenzyl)piperazine hydrochloride (33.6 mg, 0.135 mmol) and N-ethyl-N-isopropylpropan-2-amine (59.0 μl, 0.338 mmol) in dioxane (0.40 mL) was heated at 60° C. overnight. The mixture was purified by HPLC Method A to give the title compound as its TFA salt (43 mg, 97% yield) as a white solid. 1H NMR (400 MHz, methanol-d4) δ ppm 1.35 (d, J=6.83 Hz, 6H), 2.73 (s, 3H), 3.57 (br. s., 8H), 4.48 (s, 2H), 4.66 (quin, J=6.59 Hz, 1H), 7.11-7.24 (m, 2H), 7.61 (s, 1H), 7.68 (td, J=8.54, 6.35 Hz, 1H), 8.83 (s, 1H); ESI-MS m/z [M+H]+ 413.0.

Example 2 3-(4-(2,4-difluorophenoxy)piperidin-1-yl)-N-isopropyl-7-methylpyrido[3,4-b]pyrazin-2-amine

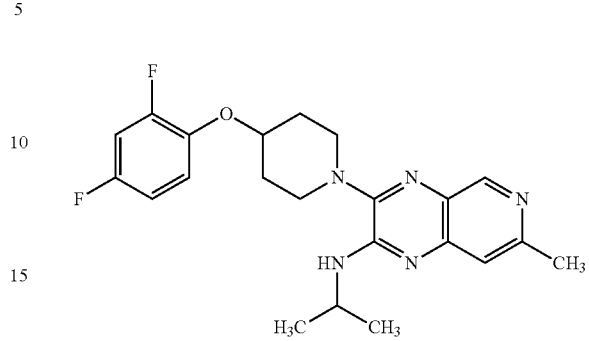

The title compound was prepared and purified in a manner similar to the preparation of Example 1 using 4-(2,4-difluorophenoxy)piperidine hydrochloride in place of 1-(2,4-difluorobenzyl)piperazine hydrochloride. The title compound was obtained as its TFA salt (44% yield) as an off-white solid. 1H NMR (400 MHz, methanol-d4) δ ppm 1.35 (d, J=6.35 Hz, 6H), 1.99 (m, 2H), 2.12-2.22 (m, 2H), 2.71 (s, 3H), 3.45 (ddd, J=13.06, 7.69, 3.66 Hz, 2H), 3.74-3.83 (m, 2H), 4.58 (tt, J=6.83, 3.42 Hz, 1H), 4.64 (quin, J=6.71 Hz, 1H), 6.90 (dddd, J=9.34, 7.87, 3.05, 1.71 Hz, 1H), 7.00 (ddd, J=11.35, 8.66, 2.93 Hz, 1H), 7.20 (td, J=9.28, 5.37 Hz, 1H), 7.56 (s, 1H), 8.73 (s, 1H); ESI-MS m/z [M+H]+ 414.0.

Example 3 (S)-3-(4-(2,4-difluorobenzyl)piperazin-1-yl-7-methyl-N-(tetrahydrofuran-3-yl)pyrido[3,4-b]pyrazin-2-amine

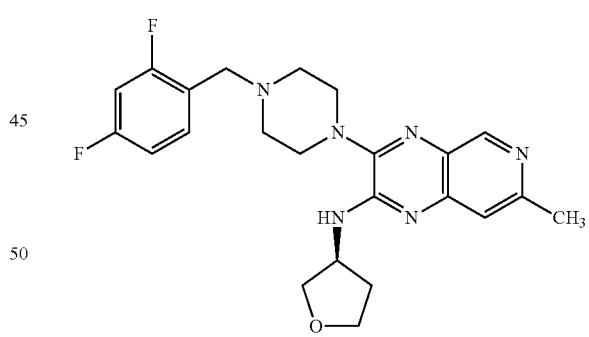

The title compound was prepared and purified in a manner similar to the preparation of Example 1 by coupling 1-(2,4-difluorobenzyl)piperazine hydrochloride and (S)-3-chloro-7-methyl-N-(tetrahydrofuran-3-yl)pyrido[3,4-b]pyrazin-2-amine. The title compound was obtained as its TFA salt (91% yield) as a white solid. 1H NMR (400 MHz, methanol-d4) δ ppm 2.09-2.18 (m, 1H), 2.42 (dtd, J=12.94, 8.18, 8.18, 6.35 Hz, 1H), 2.75 (s, 3H), 3.43-3.75 (m, 8H), 3.81-3.93 (m, 2H), 4.00-4.11 (m, 2H), 4.48 (s, 2H), 4.90-4.94 (m, 1H), 7.12-7.23 (m, 2H), 7.62-7.71 (m, 1H), 7.68 (s, 1H), 8.89 (s, 1H); ESI-MS m/z [M+H]+ 442.0.

Example 4 (S)-3-(4-(2,4-difluorophenoxy)piperidin-1-yl)-7-methyl-N-(tetrahydrofuran-3-yl)pyrido[3,4-b]pyrazin-2-amine

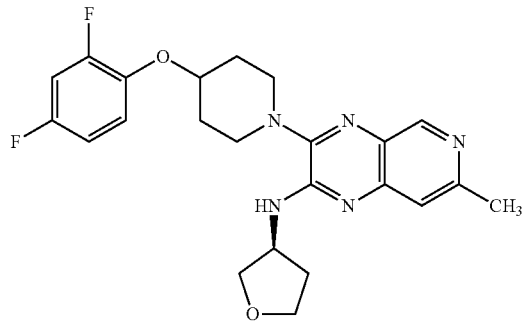 [SMILES: Cc1cc2nc(N[C@H]3CCOC3)c(N3CCC(Oc4ccc(F)cc4F)CC3)nc2cn1]

The title compound was prepared and purified in a manner similar to the preparation of Example 1 by coupling 4-(2,4-difluorophenoxy)piperidine hydrochloride and (S)-3-chloro-7-methyl-N-(tetrahydrofuran-3-yl)pyrido[3,4-b]pyrazin-2-amine. The title compound was obtained as its TFA salt (72% yield) as a white solid. 1H NMR (400 MHz, methanol-d4) δ ppm 1.92-2.04 (m, 2H), 2.15-1.98 (m, 3H), 2.42 (dtd, J=13.06, 8.12, 8.12, 6.35 Hz, 1H), 2.73 (s, 3H), 3.44-3.55 (m, 2H), 3.76-3.93 (m, 4H), 4.01-4.11 (m, 2H), 4.58 (dt, J=6.96, 3.60 Hz, 1H), 4.88-4.92 (m, 1H), 6.85-6.93 (m, 1H), 7.00 (ddd, J=11.23, 8.54, 3.17 Hz, 1H), 7.20 (td, J=9.28, 5.37 Hz, 1H), 7.62 (s, 1H), 8.79 (s, 1H); ESI-MS m/z [M+H]+ 442.0.

Example 5 (R)-3-(4-(2,4-difluorophenoxy)piperidin-1-yl)-7-methyl-N-(tetrahydrofuran-3-yl)pyrido[3,4-b]pyrazin-2-amine

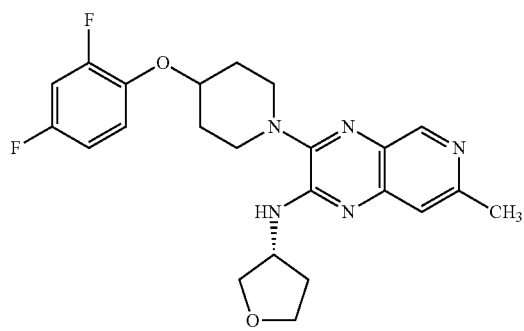 [SMILES: Cc1cc2nc(N[C@@H]3CCOC3)c(N3CCC(Oc4ccc(F)cc4F)CC3)nc2cn1]

The title compound was prepared and purified in a manner similar to the preparation of Example 1 by coupling 4-(2,4-difluorophenoxy)piperidine hydrochloride and racemic 3-chloro-7-methyl-N-(tetrahydrofuran-3-yl)pyrido[3,4-b]pyrazin-2-amine. SFC purification of the racemic product provided the free base of the title compound (11%) as a white solid. 1H NMR (400 MHz, methanol-d4) δ ppm 1.93-2.12 (m, 3H), 2.13-2.24 (m, 2H), 2.40 (ddt, J=14.40, 7.81, 6.71, 6.71 Hz, 1H), 2.58 (s, 3H), 3.14-3.29 (m, 2H), 3.53-3.67 (m, 2H), 3.81 (dd, J=9.03, 3.66 Hz, 1H), 3.88 (td, J=8.30, 5.86 Hz, 1H), 3.99-4.04 (m, 1H), 4.06 (dd, J=9.28, 5.86 Hz, 1H), 4.48-4.58 (m, 1H), 4.74 (ddt, J=7.81, 5.86, 3.91, 3.91 Hz, 1H), 6.84-6.92 (m, 1H), 6.99 (ddd, J=11.23, 8.54, 3.17 Hz, 1H), 7.20 (td, J=9.28, 5.37 Hz, 1H), 7.34 (s, 1H), 8.70 (s, 1H); ESI-MS m/z [M+H]+ 442.0.

Example 6 (R)-3-(4-(2,4-difluorobenzyl)piperazin-1-yl)-7-methyl-N-(tetrahydrofuran-3-yl)pyrido[3,4-b]pyrazin-2-amine

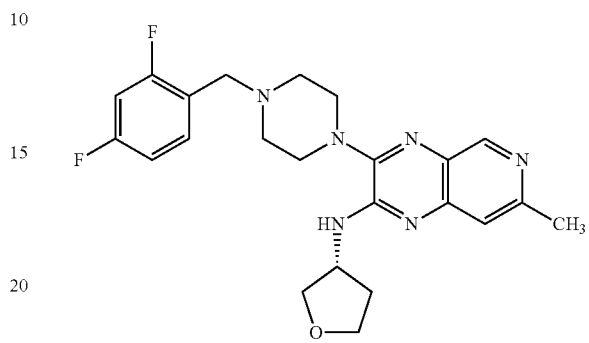

The title compound was prepared and purified in a manner similar to the preparation of Example 1 by coupling 1-(2,4-difluorobenzyl)piperazine hydrochloride and racemic 3-chloro-7-methyl-N-(tetrahydrofuran-3-yl)pyrido[3,4-b]pyrazin-2-amine. SFC purification of the racemic product provided the TFA salt of the title compound (39%) as a white solid. 1H NMR (400 MHz, methanol-d4) δ ppm 1.92-2.11 (m, 1H) 2.34-2.44 (m, 1H) 2.58 (s, 3H) 2.74 (t, J=4.39 Hz, 4H) 3.33-3.40 (m, 4H) 3.68 (s, 2H) 3.79 (dd, J=9.28, 3.91 Hz, 1H) 3.87 (td, J=8.42, 6.10 Hz, 1H) 3.98-4.02 (m, 1H) 4.04 (dd, J=9.28, 5.86 Hz, 1H) 4.73 (ddt, J=7.57, 5.86, 4.03, 4.03 Hz, 1H) 6.89-7.01 (m, 2H) 7.33 (s, 1H) 7.45-7.53 (m, 1H) 8.68 (s, 1H); ESI-MS m/z [M+H]+ 442.0.

Example 7 N-cyclopropyl-3-(4-(2,4-difluorobenzyl)piperazin-1-yl)-7-methylpyrido[3,4-b]pyrazin-2-amine

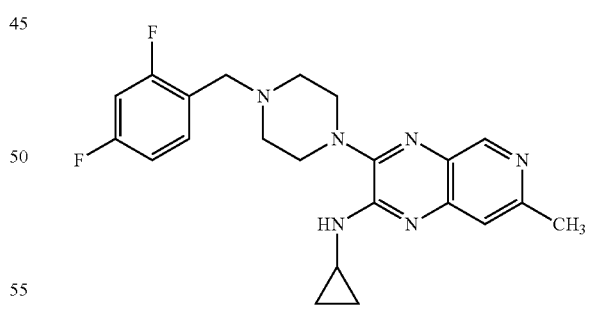

The title compound was prepared and purified in a manner similar to the preparation of Example 1 by coupling 1-(2,4-difluorobenzyl)piperazine hydrochloride and 3-chloro-N-cyclopropyl-7-methylpyrido[3,4-b]pyrazin-2-amine. The title compound was obtained as its TFA salt (22% yield) as a white solid film. 1H NMR (500 MHz, methanol-d4) δ ppm 0.77-0.86 (m, 2H) 0.94-1.04 (m, 2H) 2.75 (s, 3H) 3.13 (tt, J=7.44, 3.78 Hz, 1H) 3.54 (br. s., 8H) 4.48 (s, 2H) 7.12-7.25 (m, 2H) 7.66 (td, J=8.54, 6.35 Hz, 1H) 7.71 (s, 1H) 8.88 (s, 1H); ESI-MS m/z [M+H]+ 411.0.

Example 8 N-cyclopropyl-3-(4-(2-fluoro-4-methoxyphenoxy)piperidin-1-yl)-7-methylpyrido[3,4-b]pyrazin-2-amine 2,2,2-trifluoroacetate

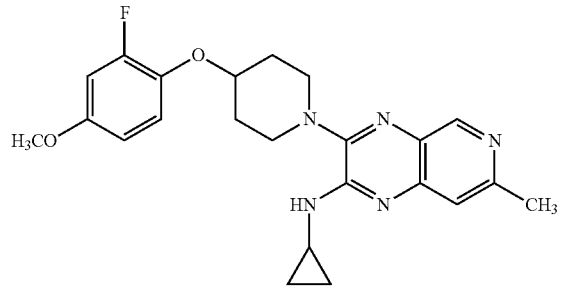 [SMILES: COc1ccc(OC2CCN(c3nc4cnc(C)cc4nc3NC3CC3)CC2)c(F)c1]

The title compound was prepared and purified in a manner similar to the preparation of Example 1 by coupling 4-(2-fluoro-4-methoxyphenoxy)piperidine hydrochloride and 3-chloro-N-cyclopropyl-7-methylpyrido[3,4-b]pyrazin-2-amine. The title compound was obtained as its TFA salt (85% yield) as a white solid. 1H NMR (400 MHz, methanol-d4) δ ppm 0.78-0.83 (m, 2H) 0.94-0.99 (m, 2H) 1.89-1.99 (m, 2H) 2.07-2.14 (m, 2H) 2.72 (s, 3H) 3.11 (tt, J=7.44, 3.78 Hz, 1H) 3.37-3.43 (m, 2H) 3.71-3.78 (m, 5H) 4.43 (tt, J=6.83, 3.42 Hz, 1H) 6.67 (ddd, J=9.28, 2.93, 1.46 Hz, 1H) 6.74 (dd, J=12.69, 2.93 Hz, 1H) 7.07 (t, J=9.28 Hz, 1H) 7.63 (s, 1H) 8.76 (s, 1H); ESI-MS m/z [M+H]+ 424.0.

Example 9 cis-3-((3-(4-(2,4-difluorophenoxy)piperidin-1-yl)-7-methylpyrido[3,4-b]pyrazin-2-yl)amino)cyclobutanol

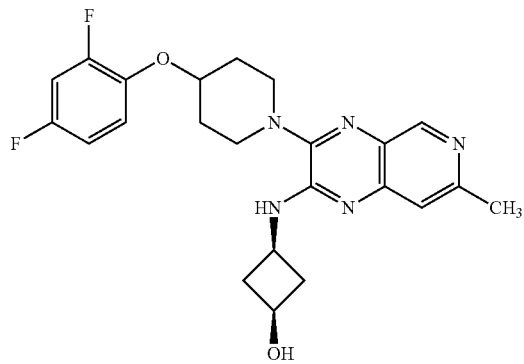 [SMILES: Cc1cc2nc(N[C@H]3C[C@@H](O)C3)c(N3CCC(Oc4ccc(F)cc4F)CC3)nc2cn1]

The title compound was prepared and purified in a manner similar to the preparation of Example 1 by coupling 4-(2,4-difluorophenoxy)piperidine hydrochloride and (1,3-cis)-3-((3-chloro-7-methylpyrido[3,4-b]pyrazin-2-yl)amino)cyclobutanol. The title compound was obtained as its TFA salt (4.1% yield) as a white solid. 1H NMR (400 MHz, methanol-d4) δ ppm 1.95-2.10 (m, 4H), 2.16-2.24 (m, 2H), 2.58 (s, 3H), 2.83-2.92 (m, 2H), 3.22-3.29 (m, 2H), 3.58-3.66 (m, 2H), 4.07-4.14 (m, 1H), 4.19 (tt, J=8.91, 6.96 Hz, 1H), 4.55 (tt, J=7.32, 3.66 Hz, 1H), 6.84-6.94 (m, 1H), 7.01 (ddd, J=11.23, 8.30, 2.93 Hz, 1H), 7.21 (td, J=9.28, 5.37 Hz, 1H), 7.32 (s, 1H), 8.68 (s, 1H); ESI-MS m/z [M+H]+ 441.9.

Example 10 cis-3-((3-(4-(2,4-difluorobenzyl)piperazin-1-yl)-7-methylpyrido[3,4-b]pyrazin-2-yl)amino)cyclobutanol

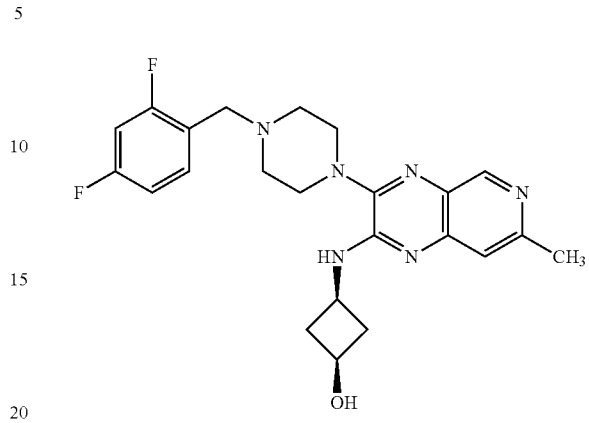

The title compound was prepared and purified in a manner similar to the preparation of Example 1 by coupling 1-(2,4-difluorobenzyl)piperazine hydrochloride and (1,3-cis)-3-((3-chloro-7-methylpyrido[3,4-b]pyrazin-2-yl)amino)cyclobutanol. The title compound was obtained as its TFA salt (5.0% yield) as a white solid. 1H NMR (400 MHz, methanol-d4) δ ppm 1.96-2.01 (m, 2H), 2.58 (s, 3H), 2.77 (t, J=4.88 Hz, 4H), 2.86 (dtd, J=9.28, 6.83, 6.83, 2.93 Hz, 2H), 3.36 (s, 1H), 3.38 (br. s., 4H), 3.70 (s, 2H), 4.06-4.13 (m, 1H), 4.17 (tt, J=8.97, 7.14 Hz, 1H), 6.89-7.06 (m, 2H), 7.32 (s, 1H), 7.50 (td, J=8.54, 6.35 Hz, 1H), 8.66 (s, 1H); ESI-MS m/z [M+H]+ 441.0.

Example 11 trans-3-(4-(2,4-difluorophenoxy)piperidin-1-yl)-N-(3-fluorocyclobutyl)-7-methylpyrido-[3,4-b]pyrazin-2-amine

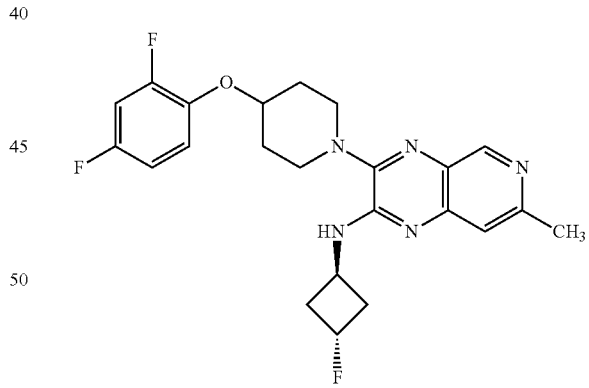

To a solution of (1,3-cis)-3-((3-(4-(2,4-difluorophenoxy)piperidin-1-yl)-7-methylpyrido[3,4-b]pyrazin-2-yl)amino)cyclobutanol (50 mg, 0.113 mmol) in DCM (2.3 mL) was added DAST (19.45 µl, 0.147 mmol) at 0° C. After the reaction was stirred for 2 h at this temperature, the reaction was warmed up to 23° C. and stirred overnight. The reaction was quenched with ice, followed by sat. NaHCO3, and vigorously stirred for 10 min. Then the mixture was extracted with EA (10 mL×2). After the solvent was removed in vacuo, the residue was purified by HPLC Method A to give the title compound as its TFA salt (3.8 mg, 7.6% yield) as a white solid. 1H NMR (400 MHz, methanol-d4) δ ppm 1.97-2.04 (m, 2H), 2.13-2.21 (m, 2H), 2.56-2.66 (m, 2H), 2.67-2.79 (m, 2H), 2.72 (s, 3H), 3.46-3.54 (m, 2H), 3.76-3.86 (m, 2H), 4.59 (tt, J=7.02, 3.48 Hz, 1H), 4.92-5.01 (m, 1H), 5.28 (dtt, J=40, 6.22, 2.81 Hz, 1H), 6.87-6.93 (m, 1H), 7.01 (ddd, J=11.35, 8.42, 3.17 Hz, 1H), 7.20 (td, J=9.15, 5.61 Hz, 1H), 7.62 (s, 1H), 8.78 (s, 1H); ESI-MS m/z [M+H]+ 443.9.

Example 12 trans-3-(4-(2,4-difluorobenzyl)piperazin-1-yl)-N-(3-fluorocyclobutyl)-7-methylpyrido[3,4-b]pyrazin-2-amine

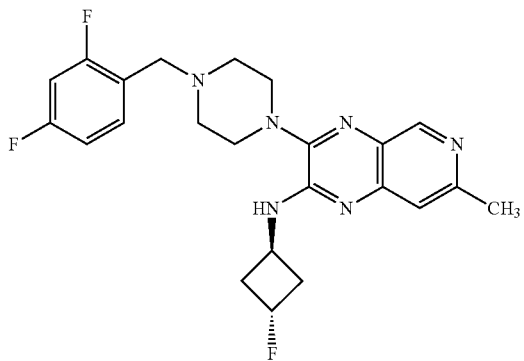 [SMILES: Cc1cc2nc(N[C@H]3C[C@H](F)C3)c(N3CCN(Cc4ccc(F)cc4F)CC3)nc2cn1]

The title compound was prepared in a manner similar to the preparation of Example using (1,3-cis)-3-((3-(4-(2,4-difluorobenzyl)piperazin-1-yl)-7-methylpyrido[3,4-b]pyrazin-2-yl)amino)cyclobutanol as the substrate. The title compound was purified by HPLC (Method A), followed by a flash chromatography column (5-10% MeOH in DCM), to furnish its free base (4.1% yield) as a white solid. 1H NMR (400 MHz, methanol-d4) δ ppm 2.48-2.57 (m, 2H), 2.58 (s, 3H), 2.64-2.72 (m, 2H), 2.72-2.78 (m, 4H), 3.37 (d, J=4.88 Hz, 4H), 3.70 (d, J=0.98 Hz, 2H), 4.77-4.83 (m, 1H), 5.14-5.36 (m, 1H), 6.92-7.14 (m, 2H), 7.34 (s, 1H), 7.50 (td, J=8.54, 6.83 Hz, 1H), 8.68 (s, 1H); ESI-MS m/z [M+H]+ 443.0.

Example 13 trans-3-((3-(4-(2,4-difluorophenoxy)piperidin-1-yl)-7-methylpyrido[3,4-b]pyrazin-2-yl)amino)cyclobutanol

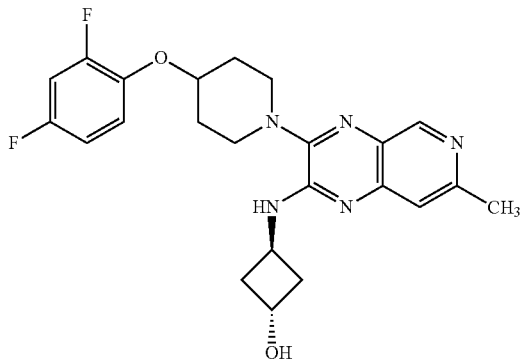 [SMILES: Cc1cc2nc(N[C@H]3C[C@H](O)C3)c(N3CCC(Oc4ccc(F)cc4F)CC3)nc2cn1]

The title compound was prepared in a manner similar to the preparation of Example 1 by coupling 4-(2,4-difluorophenoxy)piperidine hydrochloride and (1,3-trans)-3-((3-chloro-7-methylpyrido[3,4-b]pyrazin-2-yl)amino)cyclobutanol. The title compound was purified by a flash column chromatography (0-20% MeOH in DCM), to furnish its free base (80% yield) as a light yellow solid. 1H NMR (400 MHz, methanol-d4) δ ppm 2.00-2.07 (m, 2H), 2.16-2.24 (m, 2H), 2.43-2.48 (m, 4H), 2.58 (s, 3H), 3.19-3.30 (m, 2H), 3.57-3.67 (m, 2H), 4.47-4.52 (m, 1H), 4.54 (td, J=7.32, 3.42 Hz, 1H), 4.71 (quin, J=6.71 Hz, 1H), 6.86-6.93 (m, 1H), 7.00 (ddd, J=11.35, 8.42, 3.17 Hz, 1H), 7.21 (td, J=9.28, 5.37 Hz, 1H), 7.33 (s, 1H), 8.68 (s, 1H); ESI-MS m/z [M+H]+ 441.9.

Example 14 trans-3-((3-(4-(2,4-difluorobenzyl)piperazin-1-yl)-7-methylpyrido[3,4-b]pyrazin-2-yl)amino)cyclobutanol

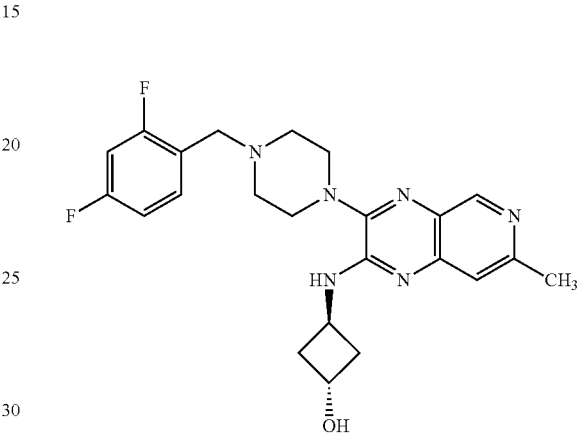

The title compound was prepared in a manner similar to the preparation of Example 1 by coupling 1-(2,4-difluorobenzyl)piperazine hydrochloride and (1,3-trans)-3-((3-chloro-7-methylpyrido[3,4-b]pyrazin-2-yl)amino)cyclobutanol. The title compound was purified by a flash column chromatography (0-20% MeOH in DCM), to furnish its free base (88% yield) as a light yellow solid. 1H NMR (400 MHz, methanol-d4) δ ppm 1.62 (dd, J=6.83, 5.86 Hz, 4H), 1.76 (s, 3H), 1.95 (t, J=4.64 Hz, 4H), 2.54-2.59 (m, 4H), 2.88 (s, 2H), 3.67 (quin, J=5.74 Hz, 1H), 3.88 (quin, J=6.83 Hz, 1H), 6.00-6.26 (m, 2H), 6.51 (s, 1H), 6.62-6.73 (m, 1H), 7.86 (s, 1H); ESI-MS m/z [M+H]+ 441.0.

Example 15 3-(4-(2,4-difluorobenzyl)piperazin-1-yl)-7-methyl-N-(oxetan-3-yl)pyrido[3,4-b]pyrazin-2-amine

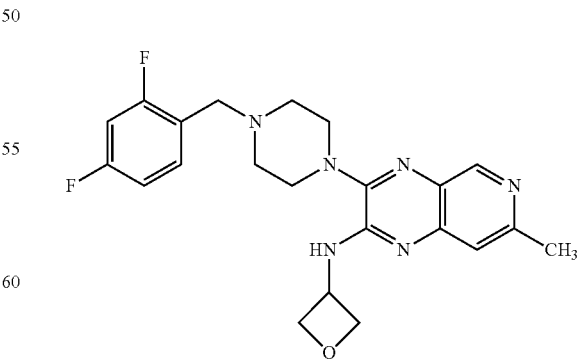

Combined 3-chloro-7-methyl-N-(oxetan-3-yl)pyrido[3,4-b]pyrazin-2-amine (26.0 mg, 0.104 mmol), 1-(2,4-difluorobenzyl)piperazine (55.0 mg, 0.259 mmol), and acetonitrile (1 mL) then added N-ethyl-N-isopropylpropan-2-amine (0.054 mL, 0.311 mmol) at 23° C. The reaction mixture was stirred at 50° C. for 7 h, cooled to 23° C., and concentrated in vacuo. The resulting residue was diluted with saturated NH4Cl (1 mL) and the crude product was extracted with EtOAc (2 mL). The organic layer was separated, washed with brine (1 mL), dried over Na2SO4, filtered, rinsed with EtOAc, and dried in vacuo. The crude material was purified by flash column chromatography using a gradient of 10-100% EtOAc in heptane to provide the free base of the title compound (37.3 mg, 84% yield) as a white solid. 1H NMR (400 MHz, DMSO-d6) δ ppm 2.51 (s, 3H), 2.68 (br. s., 4H), 3.30 (br. s., 4H), 3.64 (br. s., 2H), 4.65 (t, J=6.6 Hz, 2H), 4.81 (t, J=7.1 Hz, 2H), 4.96-5.05 (m, 1H), 7.10 (td, J=8.5, 2.4 Hz, 1H), 7.20-7.28 (m, 2H), 7.46-7.56 (m, 1H), 7.75 (d, J=4.9 Hz, 1H), 8.70 (s, 1H); ESI-MS: m/z (M+H)+ 427.0.

Example 16 3-(4-(2,4-difluorophenoxy)piperidin-1-yl)-7-methyl-N-(oxetan-3-yl)pyrido[3,4-b]pyrazin-2-amine

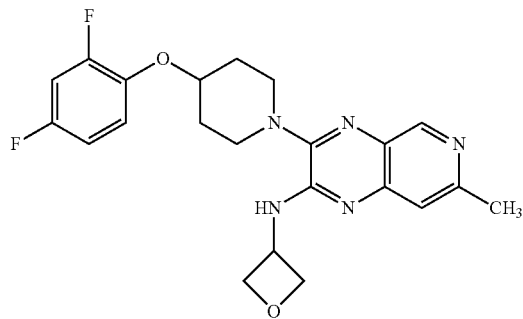 [SMILES: Cc1cc2nc(NC3COC3)c(N3CCC(Oc4ccc(F)cc4F)CC3)nc2cn1]

The title compound was prepared and purified in a manner similar to the preparation of Example 15 by using 4-(2,4-difluorophenoxy)piperidine hydrochloride to furnish its free base (66.8% yield) as an off-white solid. 1H NMR (400 MHz, DMSO-d6) δ ppm 1.93-2.00 (m, 2H), 2.14 (ddd, J=9.5, 6.3, 3.2 Hz, 2H), 2.51 (br. s., 3H), 3.16 (ddd, J=12.6, 9.4, 2.9 Hz, 2H), 3.53-3.64 (m, 2H), 4.57-4.64 (m, 1H), 4.67 (t, J=6.6 Hz, 2H), 4.83 (t, J=6.8 Hz, 2H), 4.99-5.08 (m, 1H), 7.00-7.06 (m, 1H), 7.22 (s, 1H), 7.27-7.37 (m, 2H), 7.81 (d, J=4.9 Hz, 1H), 8.70 (s, 1H); ESI-MS: m/z (M+H)+ 428.0.

Example 17 3-(4-(4-(difluoromethoxy)-2-fluorophenoxy)piperidin-1-yl)-7-methyl-N-(oxetan-3-yl)pyrido[3,4-b]pyrazin-2-amine

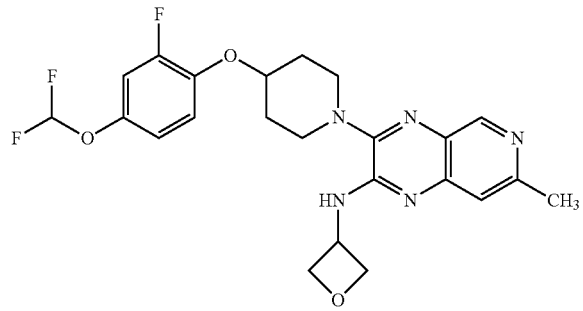 [SMILES: Cc1cc2nc(NC3COC3)c(N3CCC(Oc4ccc(OC(F)F)cc4F)CC3)nc2cn1]

The title compound was prepared and purified in a manner similar to the preparation of Example 15 by using 4-(4-(difluoromethoxy)-2-fluorophenoxy)piperidine hydrochloride to furnish its free base (71.7% yield) as an off-white solid. 1H NMR (400 MHz, DMSO-d6) δ ppm 1.91-2.03 (m, 2H), 2.15 (ddd, J=9.5, 6.1, 3.4 Hz, 2H), 2.51 (br. s., 3H), 3.11-3.22 (m, 2H), 3.53-3.64 (m, 2H), 4.61-4.70 (m, 3H), 4.83 (t, J=6.8 Hz, 2H), 4.98-5.08 (m, 1H), 6.98-7.02 (m, 1H), 7.02-7.33 (m, 3H), 7.36 (t, J=9.5 Hz, 1H), 7.81 (d, J=4.9 Hz, 1H), 8.70 (s, 1H); ESI-MS: m/z (M+H)+ 476.0.

Example 18 3-(4-(4-(difluoromethoxy)-2-fluorophenoxy)piperidin-1-yl)-N-isopropyl-7-methylpyrido[3,4-b]pyrazin-2-amine

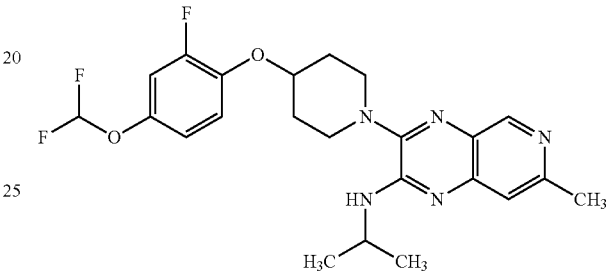

Combined 4-(4-(difluoromethoxy)-2-fluorophenoxy)piperidine hydrochloride (41 mg, 0.137 mmol), 3-chloro-N-isopropyl-7-methylpyrido[3,4-b]pyrazin-2-amine (13 mg, 0.055 mmol), and N-ethyl-N-isopropylpropan-2-amine (21 mg, 0.165) in acetonitrile (0.55 mL). The reaction vessel was sealed and heated to 90° C. for 6 h and then allowed to cool to room temperature. The crude solution was purified via HPLC using method A to give the title compound as a yellow semi-solid (11 mg, 36% yield). 1H NMR (400 MHz, CDCl3) δ ppm 1.34 (d, J=5.86 Hz, 6H), 2.05-2.13 (m, 4H), 2.81 (s, 3H), 3.63-3.65 (m, 2H), 3.83-3.87 (m, 2H), 4.34-4.35 (m, 1H), 4.57 (m, 1H), 5.08-5.10 (m, 1H), 6.47 (t, J=60 Hz, 1H), 6.96-6.97 (m, 1H), 6.97-6.99 (m, 2H), 7.53 (s, 1H), 8.98 (s, 1H); ESI-MS m/z [M+H]+ 462.4.

Example 19 N-cyclopropyl-3-(4-(4-(difluoromethoxy)-2-fluorophenoxy)piperidin-1-yl)-7-methylpyrido[3,4-b]pyrazin-2-amine

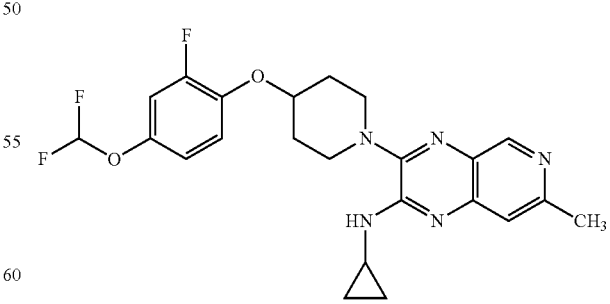

The title compound was prepared in a manner similar to Example 18 using 3-chloro-N-cyclopropyl-7-methylpyrido[3,4-b]pyrazin-2-amine and 3-chloro-N-cyclopropyl-7-methylpyrido[3,4-b]pyrazin-2-amine to give the title compound (60.4% yield) as a white solid. 1H NMR (400 MHz, DMSO-d6) δ ppm 0.80-0.86 (m, 4H), 1.86-1.88 (m, 2H), 2.07-2.09 (m, 2H), 2.64 (s, 3H), 3.11-3.12 (m, 1H), 3.29-3.31 (m, 2H), 3.64-3.67 (m, 2H), 4.67-4.68 (m, 1H), 6.99-7.36 (m, 4H), 7.65 (s, 1H), 8.45 (d, J=4.39 Hz, 1H), 8.97 (s, 1H); ESI-MS m/z [M+H]+ 460.4.

Example 20 (R)-3-(4-(4-(difluoromethoxy)-2-fluorophenoxy)piperidin-1-yl)-7-methyl-N-(tetrahydrofuran-3-yl)pyrido[3,4-b]pyrazin-2-amine

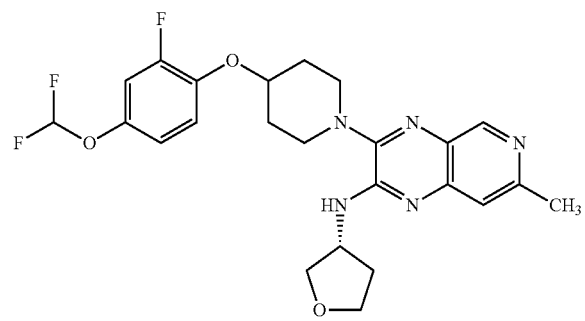 [SMILES: Cc1cc2nc(N[C@@H]3CCOC3)c(N3CCC(Oc4ccc(OC(F)F)cc4F)CC3)nc2cn1]

The title compound was prepared in a manner similar to Example 18 using (R)-3-chloro-7-methyl-N-(tetrahydrofuran-3-yl)pyrido[3,4-b]pyrazin-2-amine to give the title compound (63.2% yield) as a white solid. 1H NMR (400 MHz, DMSO-d6) δ ppm 2.08-2.09 (m, 2H), 2.10-2.11 (m, 3H), 2.35 (m, 1H), 2.64 (s, 3H), 3.33-3.37 (m, 2H), 3.71-3.75 (m, 4H), 3.92-3.98 (m, 2H), 4.69-4.75 (m, 2H), 6.99-7.37 (m, 4H), 7.62 (s, 1H), 8.39 (d, J=6.35 Hz, 1H), 8.98 (s, 1H); ESI-MS m/z [M+H]+ 490.4.

Example 21 (S)-3-(4-(4-(difluoromethoxy)-2-fluorophenoxy)piperidin-1-yl)-7-methyl-N-(tetrahydrofuran-3-yl)pyrido[3,4-b]pyrazin-2-amine

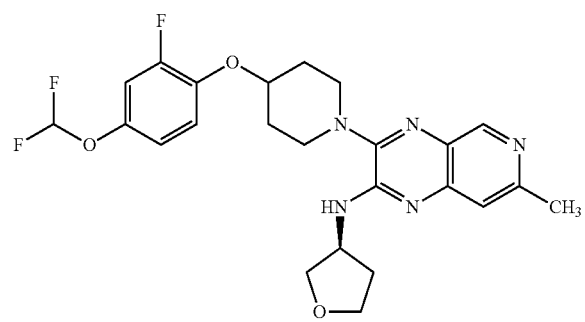 [SMILES: Cc1cc2nc(N[C@H]3CCOC3)c(N3CCC(Oc4ccc(OC(F)F)cc4F)CC3)nc2cn1]

The title compound was prepared in a manner similar to Example 18 using (S)-3-chloro-7-methyl-N-(tetrahydrofuran-3-yl)pyrido[3,4-b]pyrazin-2-amine to give the title compound (67.7% yield) as a white solid. 1H NMR (400 MHz, DMSO-d6) δ ppm 2.08-2.09 (m, 2H), 2.10-2.11 (m, 3H), 2.35 (m, 1H), 2.64 (s, 3H), 3.33-3.37 (m 2H), 3.71-3.75 (m, 4H), 3.78-3.98 (m, 2H), 4.69-4.75 (m, 2H), 6.99-7.37 (m, 4H), 7.62 (s, 1H), 8.39 (d, J=6.35 Hz, 1H), 8.98 (s, 1H); ESI-MS m/z [M+H]+ 490.4.

Example 22 3-(4-(2-fluoro-4-methoxy benzyl)piperazin-1-yl)-N-isopropyl-7-methylpyrido[3,4-b]pyrazin-2-amine

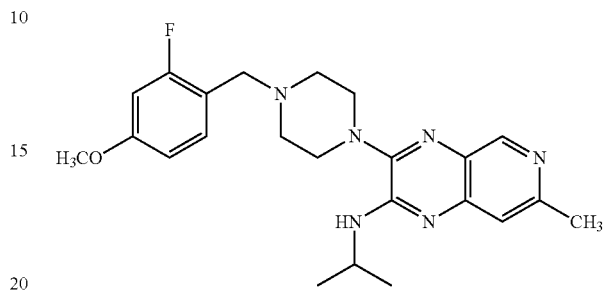

Combined 1-(2-fluoro-4-methoxybenzyl)piperazine TFA (44 mg, 0.137 mmol), 3-chloro-N-isopropyl-7-methylpyrido[3,4-b]pyrazin-2-amine (13 mg, 0.055 mmol), and N-ethyl-N-isopropylpropan-2-amine (21 mg, 0.165 mmol) in acetonitrile (0.55 mL). The reaction vessel was sealed and heated to 90° C. for 8 h and then allowed to cool to room temperature. The crude solution was purified by HPLC using method B to give the title compound as a white solid (4 mg, 17% yield). 1H NMR (400 MHz, DMSO-d6) δ ppm 1.24 (d, J=6.83 Hz, 6H), 2.64 (s, 3H), 3.23-3.28 (m, 4H), 3.30-3.36 (m, 4H), 3.58 (s, 2H), 3.77 (s, 3H), 4.35-4.39 (m, 1H), 6.79-6.83 (m, 3H), 7.24 (s, 1H), 7.34 (m, 1H), 8.66 (s, 1H); ESI-MS m/z [M+H]+ 425.6.

Example 23 N-cyclopropyl-3-(4-(2-fluoro-4-methoxybenzyl)piperazin-1-yl)-7-methylpyrido[3,4-b]pyrazin-2-amine

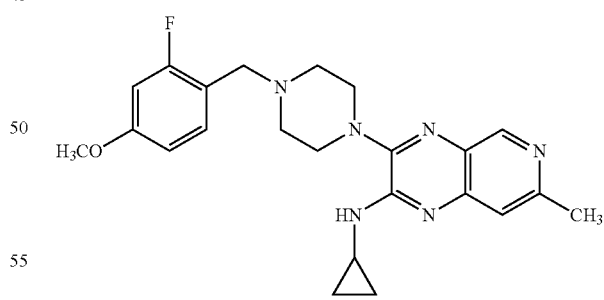

The title compound was prepared and purified in a manner similar to Example 22 using 3-chloro-N-cyclopropyl-7-methylpyrido[3,4-b]pyrazin-2-amine to give the title compound as a white solid (27.8% yield). 1H NMR (400 MHz, DMSO-d6) δ ppm 0.66-0.67 (m, 2H), 0.76-0.79 (m, 2H), 2.62 (s, 3H), 2.89 (dd, J=7.32, 3.91 Hz, 1H), 3.18-3.20 (m, 4H), 3.30-3.34 (m, 4H), 3.56 (s, 2H), 3.77 (s, 3H), 6.77-6.83 (m, 2H), 7.20 (d, J=2.93 Hz, 1H), 7.29-7.34 (m, 2H), 8.68 (s, 1H); ESI-MS m/z [M+H]+ 423.5.

Example 24 (R)-3-(4-(2-fluoro-4-methoxy benzyl)piperazin-1-yl)-7-methyl-N-(tetrahydrofuran-3-yl)pyrido[3,4-b]pyrazin-2-amine

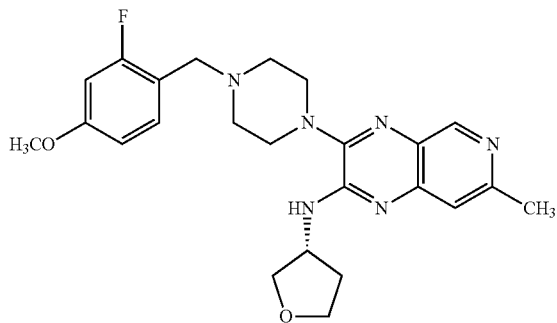 [SMILES: COc1ccc(CN2CCN(c3nc4cnc(C)cc4nc3N[C@@H]3CCOC3)CC2)c(F)c1]

The title compound was prepared and purified in a manner similar to Example 22 using (R)-3-chloro-7-methyl-N-(tetrahydrofuran-3-yl)pyrido[3,4-b]pyrazin-2-amine to give the title compound (39% yield) as a white solid. 1H NMR (400 MHz, DMSO-d6) δ ppm 2.03-2.05 (m, 1H), 2.23-2.25 (m, 1H), 2.64 (s, 3H), 3.23-3.25 (m, 4H), 3.30-3.34 (m, 4H), 3.57 (s, 2H), 3.66-3.67 (m, 1H), 3.75-3.76 (m, 1H), 3.77 (s, 3H), 3.88-3.89 (m, 1H), 3.95-3.96 (m, 1H), 4.59-4.62 (m, 1H), 6.77-6.82 (m, 2H), 7.01 (d, J=6.35 Hz, 1H), 7.25 (s, 1H), 7.33-7.35 (m, 1H), 8.68 (s, 1H); ESI-MS m/z [M+H]+ 453.4.

Example 25 (S)-3-(4-(2-fluoro-4-methoxybenzyl)piperazin-1-yl)-7-methyl-N-(tetrahydrofuran-3-yl)pyrido[3,4-b]pyrazin-2-amine

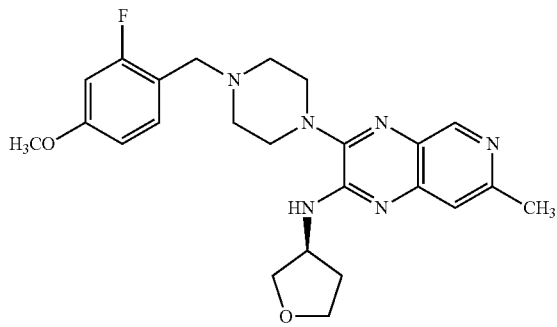

The title compound was prepared and purified in a manner similar to Example 22 using (S)-3-chloro-7-methyl-N-(tetrahydrofuran-3-yl)pyrido[3,4-b]pyrazin-2-amine to give the title compound (39% yield) as a white solid. 1H NMR (400 MHz, DMSO-d6) δ ppm 2.03-2.05 (m, 1H), 2.23-2.25 (m, 1H), 2.64 (s, 3H), 3.23-3.25 (m, 4H), 3.30-3.34 (m, 4H), 3.57 (s, 2H), 3.64-3.66 (m, 1H), 3.67-3.69 (m, 1H), 3.77 (s, 3H), 3.92-3.94 (m, 1H), 3.95-3.96 (m, 1H), 4.59-4.63 (m, 1H), 6.77-6.82 (m, 2H), 7.01 (d, J=5.86 Hz, 1H), 7.25 (s, 1H), 7.33-7.35 (m, 1H), 8.68 (s, 1H); ESI-MS m/z [M+H]+ 453.4.

Example 26 3-(4-(4-(difluoromethoxy)-2-fluorobenzyl)piperazin-1-yl)-N-isopropyl-7-methylpyrido[3,4-b]pyrazin-2-amine

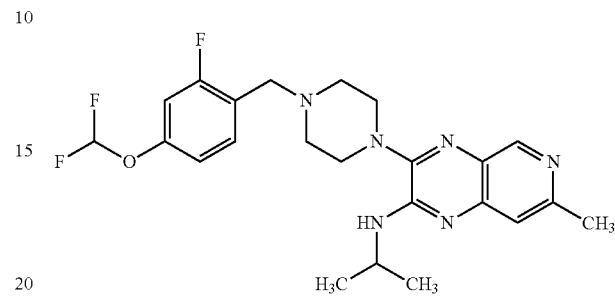

The title compound was prepared in a manner similar to Example 22 using 3-chloro-N-isopropyl-7-methylpyrido[3,4-b]pyrazin-2-amine and 1-(4-(difluoromethoxy)-2-fluorobenzyl)piperazine hydrochloride. The title compound was purified by HPLC using Method B to give its free base (75% yield) as a light yellow solid. 1H NMR (400 MHz, DMSO-d6) δ ppm 1.24 (d, J=6.8 Hz, 6H), 2.50 (s, 3H), 2.60-2.74 (m, 4H), 3.23 (br. s., 4H), 3.63 (s, 2H), 4.31-4.43 (m, 1H), 6.73 (d, J=8.3 Hz, 1H), 7.05 (dd, J=8.5, 2.2 Hz, 1H), 7.13 (dd, J=10.7, 2.4 Hz, 1H), 7.15-7.46 (m, 2H), 7.51 (t, J=8.5 Hz, 1H), 8.66 (s, 1H); ESI-MS: m/z (M+H)+ 461.0.

Example 27 N-cyclopropyl-3-(4-(4-(difluoromethoxy)-2-fluorobenzyl)piperazin-1-yl)-7-methylpyrido[3,4-b]pyrazin-2-amine

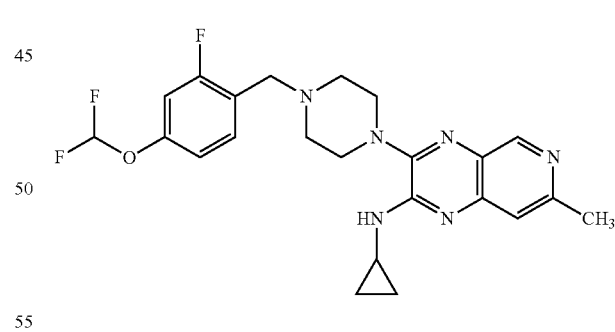

The title compound was prepared in a manner similar to Example 22 using 3-chloro-N-cyclopropyl-7-methylpyrido[3,4-b]pyrazin-2-amine and 1-(4-(difluoromethoxy)-2-fluorobenzyl)piperazine hydrochloride. The title compound was purified by HPLC using Method B to give its free base (85% yield) as an off-white solid. 1H NMR (400 MHz, DMSO-d6) δ ppm 0.62-0.72 (m, 2H), 0.72-0.82 (m, 2H), 2.52 (s, 3H), 2.57-2.76 (m, 4H), 2.90 (tq, J=7.3, 3.8 Hz, 1H), 3.21 (br. s., 4H), 3.63 (br. s., 2H), 7.05 (dd, J=8.5, 2.2 Hz, 1H), 7.13 (dd, J=11.0, 2.2 Hz, 1H), 7.15-7.46 (m, 3H), 7.50 (t, J=8.3 Hz, 1H), 8.70 (s, 1H); ESI-MS: m/z (M+H)+ 459.0.

Example 28 (R)-3-(4-(4-(difluoromethoxy)-2-fluorobenzyl)piperazin-1-yl)-7-methyl-N-(tetrahydrofuran-3-yl)pyrido[3,4-b]pyrazin-2-amine

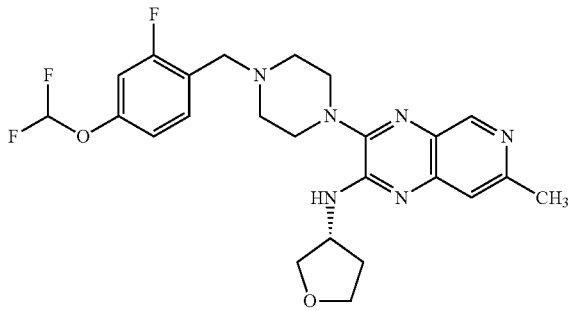 [SMILES: Cc1cc2nc(N[C@@H]3CCOC3)c(N3CCN(Cc4ccc(OC(F)F)cc4F)CC3)nc2cn1]

The title compound was prepared in a manner similar to Example 22 using (R)-3-chloro-7-methyl-N-(tetrahydrofuran-3-yl)pyrido[3,4-b]pyrazin-2-amine and 1-(4-(difluoromethoxy)-2-fluorobenzyl)piperazine hydrochloride. The title compound was purified by HPLC using Method B to give its free base (61.4% yield) as a light yellow solid. 1H NMR (400 MHz, DMSO-d6) δ ppm 2.00-2.08 (m, 1H), 2.19-2.28 (m, 1H), 2.51 (s, 3H), 2.58-2.81 (m, 4H), 3.27 (br. s., 4H), 3.58-3.70 (m, 3H), 3.74 (td, J=8.2, 6.1 Hz, 1H), 3.85-3.92 (m, 1H), 3.95 (dd, J=8.8, 6.3 Hz, 1H), 4.58-4.66 (m, 1H), 7.05 (dd, J=8.5, 2.2 Hz, 1H), 7.09 (d, J=5.4 Hz, 1H), 7.14 (dd, J=11.0, 2.2 Hz, 1H), 7.15-7.46 (m, 2H), 7.51 (t, J=8.5 Hz, 1H), 8.70 (s, 1H); ESI-MS: m/z (M+H)+ 489.0.

Example 29 (S)-3-(4-(4-(difluoromethoxy)-2-fluorobenzyl)piperazin-1-yl)-7-methyl-N-(tetrahydrofuran-3-yl)pyrido[3,4-b]pyrazin-2-amine

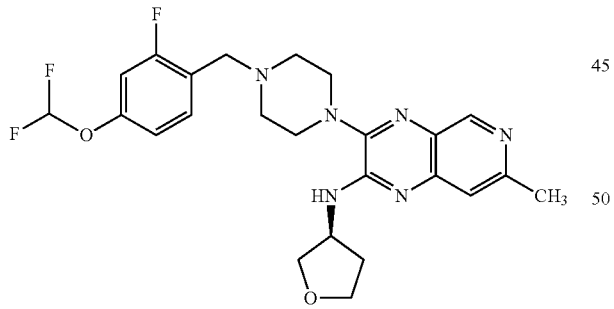

The title compound was prepared in a manner similar to Example 22 using (S)-3-chloro-7-methyl-N-(tetrahydrofuran-3-yl)pyrido[3,4-b]pyrazin-2-amine and 1-(4-(difluoromethoxy)-2-fluorobenzyl)piperazine hydrochloride. The title compound was purified by HPLC using Method B to give its free base (63.6% yield) as a light yellow solid. 1H NMR (400 MHz, DMSO-d6) δ ppm 2.00-2.08 (m, 1H), 2.23 (dtd, J=12.7, 7.8, 7.8, 6.3 Hz, 1H), 2.52 (s, 3H), 2.55-2.96 (m, 4H), 3.27 (br. s., 4H), 3.53-3.70 (m, 3H), 3.74 (td, J=8.1, 5.9 Hz, 1H), 3.85-3.92 (m, 1H), 3.95 (dd, J=8.8, 6.3 Hz, 1H), 4.57-4.67 (m, 1H), 7.05 (dd, J=8.3, 2.0 Hz, 1H), 7.08-7.47 (m, 4H), 7.52 (t, J=8.5 Hz, 1H), 8.70 (s, 1H); ESI-MS: m/z (M+H)+ 489.0.

Example 30 2-(4-(2,4-difluorobenzyl)piperazin-1-yl)-N-isopropyl-7-methylpyrido[3,4-b]pyrazin-3-amine 2,2,2-trifluoroacetate

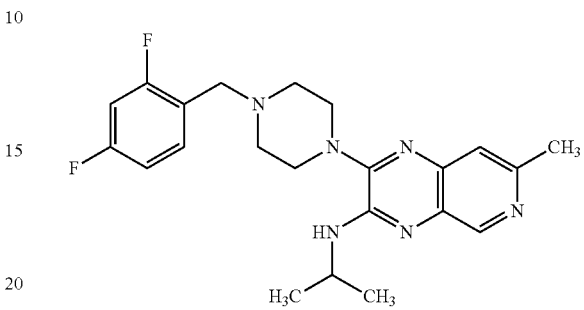

A solution of 3-chloro-2-(4-(2,4-difluorobenzyl)piperazin-1-yl)-7-methylpyrido[3,4-b]pyrazine (15 mg, 0.038 mmol), propan-2-amine (29.7 μl, 0.345 mmol) and DIPEA (20.12 μl, 0.115 mmol) in MeCN (0.19 mL) was heated at 90° C. overnight. The title compound was purified by HPLC using Method A to furnish its TFA salt (16.0 mg, 79% yield) as a white solid. 1H NMR (400 MHz, methanol-d4) δ ppm 1.33 (d, J=6.83 Hz, 7H), 2.75 (s, 3H), 3.54 (br. s., 4H), 4.03 (br. s., 4H), 4.36-4.57 (m, 3H), 7.05-7.25 (m, 2H), 7.66 (td, J=8.54, 6.35 Hz, 1H), 7.78 (s, 1H), 8.82 (s, 1H); ESI-MS m/z [M+H]+ 413.0.

Example 31 N-cyclopropyl-2-(4-(2,4-difluorobenzyl)piperazin-1-yl)-7-methylpyrido[3,4-b]pyrazin-3-amine 2,2,2-trifluoroacetate

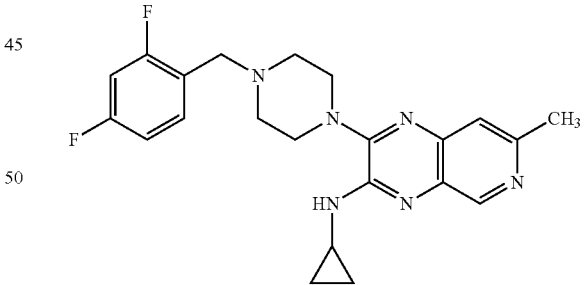

The title compound was prepared and purified in a manner similar to the preparation of Example 30 by coupling 3-chloro-2-(4-(2,4-difluorobenzyl)piperazin-1-yl)-7-methylpyrido[3,4-b]pyrazine and 10 equivalents of cyclopropanamine at 110° C. The title compound was obtained as its TFA salt (15.9% yield) as a yellow solid. 1H NMR (400 MHz, methanol-d4) δ ppm 0.64-0.78 (m, 2H) 0.85-0.96 (m, 2H) 2.76 (s, 4H) 2.89-2.98 (m, 1H) 3.51 (br. s., 5H) 3.84-4.16 (m, 4H) 4.46 (s, 3H) 7.01-7.24 (m, 2H) 7.65 (td, J=8.42, 6.10 Hz, 1H) 7.81 (s, 1H) 8.91 (s, 1H); ESI-MS m/z [M+H]+ 411.0.

Example 32 (S)-2-(4-(2,4-difluorobenzyl)piperazin-1-yl)-7-methyl-N-(tetrahydrofuran-3-yl)pyrido[3,4-b]pyrazin-3-amine

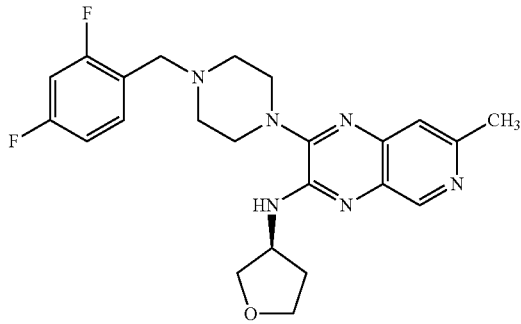 [SMILES: Cc1cc2nc(N3CCN(Cc4ccc(F)cc4F)CC3)c(N[C@H]3CCOC3)nc2cn1]

The title compound was prepared in a manner similar to Example 30 using (S)-tetrahydrofuran-3-amine hydrochloride and 3-chloro-2-(4-(2,4-difluorobenzyl)piperazin-1-yl)-7-methylpyrido[3,4-b]pyrazine to give the title compound (14.8% yield) as a white solid. 1H NMR (400 MHz, MeOD-d4) δ ppm 2.03-2.05 (m, 1H), 2.38-2.40 (m, 1H), 2.58 (s, 3H), 2.65-2.77 (m, 4H), 3.41-3.58 (m, 4H), 3.66 (s, 2H), 3.79 (dd, J=9.28, 3.91 Hz, 1H), 3.86 (m, 1H), 3.87 (m, 1H), 4.06 (dd, J=9.28, 5.86 Hz, 1H), 4.69 (m, 1H), 6.91-7.01 (m, 2H), 7.39 (s, 1H), 7.49 (m, 1H), 8.69 (s, 1H); ESI-MS m/z [M+H]+ 441.4.

Example 33 (R)-2-(4-(2,4-difluorobenzyl)piperazin-1-yl-7-methyl-N-(tetrahydrofuran-3-yl)pyrido[3,4-b]pyrazin-3-amine

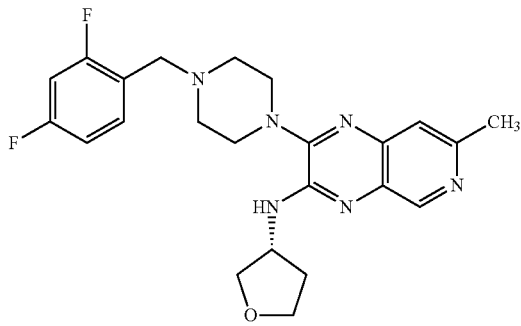 [SMILES: Cc1cc2nc(N3CCN(Cc4ccc(F)cc4F)CC3)c(N[C@@H]3CCOC3)nc2cn1]

The title compound was prepared in a manner similar to Example 30 using (R)-tetrahydrofuran-3-amine hydrochloride and 3-chloro-2-(4-(2,4-difluorobenzyl)piperazin-1-yl)-7-methylpyrido[3,4-b]pyrazine to give the title compound (8.9% yield) as a white solid. 1H NMR (400 MHz, MeOD-d4) δ ppm 2.02-2.03 (m, 1H), 2.36-2.37 (m, 1H), 2.58 (s, 3H), 2.68-2.73 (m, 4H), 3.45-3.66 (m, 4H), 3.79 (s, 2H), 3.80 (dd, J=9.28, 3.91 Hz, 1H), 3.86 (m, 1H), 3.87 (m, 1H), 4.06 (dd, J=9.28, 5.86 Hz, 1H), 4.69 (m, 1H), 6.94-6.98 (m, 2H), 7.40 (s, 1H), 7.47 (m, 1H), 8.68 (s, 1H); ESI-MS m/z [M+H]+ 441.4.

Example 34 N-cyclopropyl-2-(4-(2,4-difluorophenoxy)piperidin-1-yl)-7-methylpyrido[3,4-b]pyrazin-3-amine

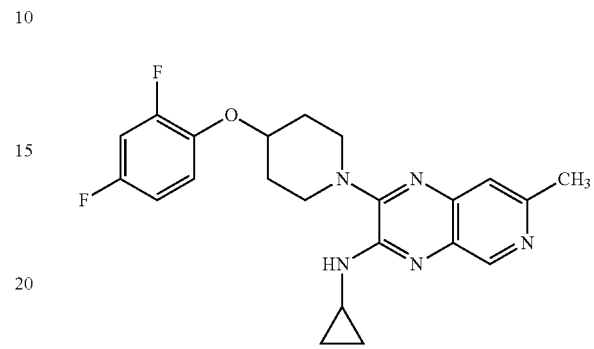

The title compound was prepared in a manner similar to Example 30 using 10 equivalents of cyclopropanamine and 3-chloro-2-(4-(2,4-difluorophenoxy)piperidin-1-yl)-7-methylpyrido[3,4-b]pyrazine at 110° C. to give the title compound (23.8% yield) as a dark yellow semi-solid. 1H NMR (400 MHz, MeOD-d4) δ ppm 0.70-0.74 (m, 2H), 0.88-0.90 (m, 2H), 2.71 (s, 3H), 2.90 (dt, J=7.44, 3.36 Hz, 1H), 3.77-3.80 (m, 2H), 3.99-4.02 (m, 2H), 4.57-4.58 (m, 1H), 6.87-6.89 (m, 1H), 6.99-7.01 (m, 1H), 7.18-7.19 (m, 1H), 7.65 (s, 1H), 8.73 (s, 1H); ESI-MS m/z [M+H]+ 412.4.

Example 35 2-(4-(2,4-difluorophenoxy)piperidin-1-yl)-N-isopropyl-7-methylpyrido[3,4-b]pyrazin-3-amine

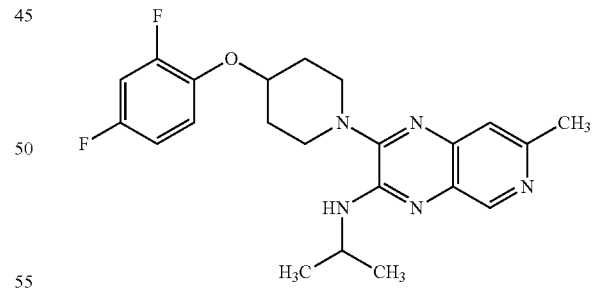

The title compound was prepared in a manner similar to Example 30 using 10 equivalents of propan-2-amine and 3-chloro-2-(4-(2,4-difluorophenoxy)piperidin-1-yl)-7-methylpyrido[3,4-b]pyrazine at 110° C. to give the title compound (15.6% yield) as a yellow solid. 1H NMR (400 MHz, MeOD-d4) δ ppm 1.32 (d, J=6.35 Hz, 6H), 1.93-1.96 (m, 2H), 2.09-2.11 (m, 2H), 2.70 (s, 3H), 3.83-3.84 (m, 2H), 4.05-4.06 (m 2H), 4.42-4.44 (m, 1H), 6.89 (m, 1H), 7.00-7.02 (m, 1H), 7.19-7.20 (m, 1H), 7.62 (s, 1H), 8.64 (s, 1H); ESI-MS m/z [M+H]+ 414.4.

Example 36 (R)-2-(4-(2,4-difluorophenoxy)piperidin-1-yl)-7-methyl-N-(tetrahydrofuran-3-yl)pyrido[3,4-b]pyrazin-3-amine

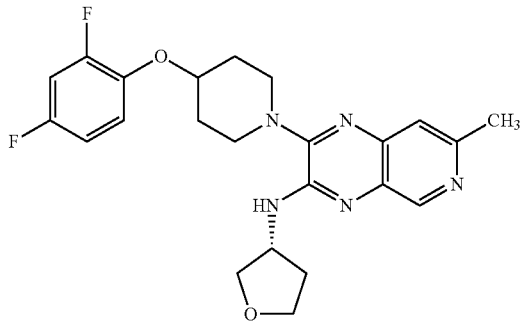 [SMILES: Cc1cc2nc(N3CCC(Oc4ccc(F)cc4F)CC3)c(N[C@@H]3CCOC3)nc2cn1]

The title compound was prepared in a manner similar to Example 30 using (R)-tetrahydrofuran-3-amine hydrochloride and 3-chloro-2-(4-(2,4-difluorophenoxy)piperidin-1-yl)-7-methylpyrido[3,4-b]pyrazine to give the title compound (11.8% yield) as a yellow solid. 1H NMR (400 MHz, MeOD-d4) δ ppm 2.08-2.09 (m, 2H), 2.10-2.12 (m, 3H), 2.35-2.36 (m, 1H), 2.71 (s, 3H), 3.82-3.86 (m 4H), 4.04-4.07 (m, 4H), 4.60 (m, 1H), 4.67 (m, 1H), 6.89 (m, 1H), 7.00-7.02 (m, 1H), 7.17-7.19 (m, 1H), 7.64 (s 1H), 8.69 (s, 1H); ESI-MS m/z [M+H]+ 442.4.

Example 37 (S)-2-(4-(2,4-difluorophenoxy)piperidin-1-yl)-7-methyl-N-(tetrahydrofuran-3-yl)pyrido[3,4-b]pyrazin-3-amine

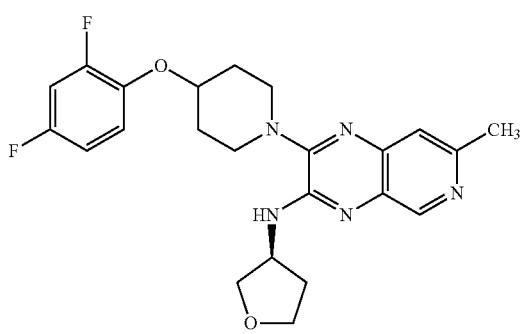 [SMILES: Cc1cc2nc(N3CCC(Oc4ccc(F)cc4F)CC3)c(N[C@H]3CCOC3)nc2cn1]

The title compound was prepared in a manner similar to Example 30 using (S)-tetrahydrofuran-3-amine 4-methylbenzenesulfonate and 3-chloro-2-(4-(2,4-difluorophenoxy)piperidin-1-yl)-7-methylpyrido[3,4-b]pyrazine to give the title compound (2.1% yield) as a yellow solid. 1H NMR (400 MHz, MeOD-d4) δ ppm 2.08-2.09 (m, 2H), 2.10-2.11 (m, 3H), 2.35-2.36 (m, 1H), 2.70 (s, 3H), 3.82-3.86 (m 4H), 4.04-4.07 (m, 4H), 4.60 (m, 1H), 4.67 (m, 1H), 6.89 (m, 1H), 7.00-7.01 (m, 1H), 7.17-7.19 (m, 1H), 7.64 (s 1H), 8.69 (s, 1H); ESI-MS m/z [M+H]+ 442.4.

Example 38 2-(4-(4-(difluoromethoxy)-2-fluorophenoxy)piperidin-1-yl)-N-isopropyl-7-methylpyrido[3,4-b]pyrazin-3-amine

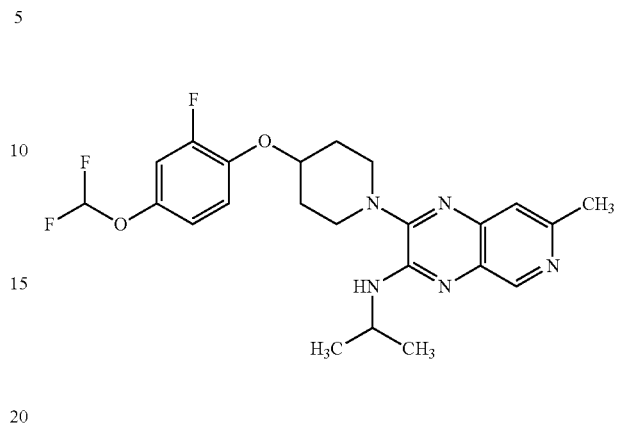

Combined 3-chloro-2-(4-(4-(difluoromethoxy)-2-fluorophenoxy)piperidin-1-yl)-7-methylpyrido[3,4-b]pyrazine (30 mg, 0.068 mmol), propan-2-amine (40 mg, 0.680 mmol), and N-ethyl-N-isopropylpropan-2-amine (132 mg, 1.02 mmol) in acetonitrile (1.00 mL). The reaction vessel was sealed and heated to 120° C. for 16 h and then allowed to cool to room temperature. The crude solution was purified by HPLC using Method A to give the title compound as a yellow solid (6 mg, 16%). 1H NMR (400 MHz, CDCl3) δ ppm 1.34 (d, J=5.86, Hz, 6H), 2.01-2.13 (m, 4H), 2.81 (m, 3H), 3.63-3.65 (m, 2H), 3.83-3.87 (m, 2H), 4.34-4.35 (m, 1H), 4.57 (m, 1H), 5.08-5.10 (m, 1H), 6.47 (t, J=60 Hz, 1H), 6.96-6.97 (m, 1H), 6.98-7.01 (m, 2H), 7.53 (s, 1H), 8.98 (s, 1H); ESI-MS m/z [M+H]+ 462.4.

Example 39 N-cyclopropyl-2-(4-(4-(difluoromethoxy)-2-fluorophenoxy)piperidin-1-yl)-7-methylpyrido[3,4-b]pyrazin-3-amine

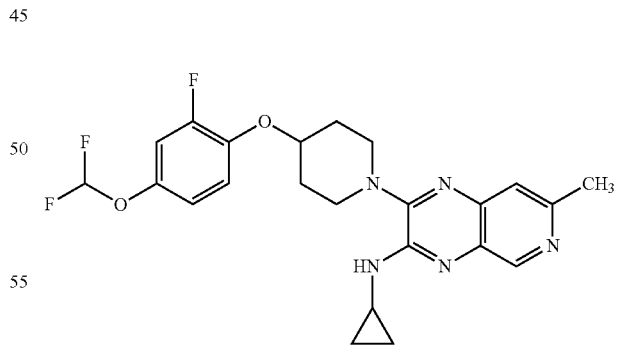

The title compound was prepared and purified in a manner similar to Example 38 using cyclopropanamine to give the title compound (18.4% yield) as a yellow film. 1H NMR (400 MHz, CDCl3) δ ppm 0.64-0.66 (m, 2H), 0.96-0.99 (m, 2H), 2.01-2.12 (m, 4H), 2.80 (m, 3H), 2.94-2.96 (m, 1H), 3.63-3.65 (m, 2H), 3.79-3.84 (m, 2H), 4.55 (dt, J=6.22, 2.99 Hz, 1H), 6.46 (t, J=70.3 Hz, 1H), 6.95-7.03 (m, 3H), 7.51 (s, 1H), 9.01 (s, 1H); ESI-MS m/z [M+H]+ 460.4.

Example 40 (R)-2-(4-(4-(difluoromethoxy)-2-fluorophenoxy)piperidin-1-yl)-7-methyl-N-(tetrahydrofuran-3-yl)pyrido[3,4-b]pyrazin-3-amine

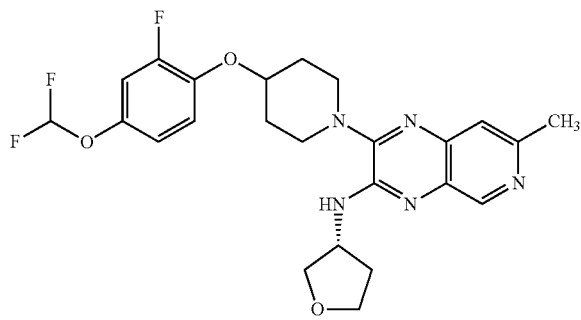 [SMILES: Cc1cc2nc(N3CCC(Oc4ccc(OC(F)F)cc4F)CC3)c(N[C@@H]3CCOC3)nc2cn1]

The title compound was prepared and purified in a manner similar to Example 38 using (R)-tetrahydrofuran-3-amine hydrochloride to give the title compound (17.4% yield) as a yellow film. 1H NMR (400 MHz, CDCl3) δ ppm 1.95-2.12 (m, 5H), 2.35-2.45 (m, 1H), 2.80 (s, 3H), 3.60-3.76 (m, 2H), 3.87-3.95 (m, 6H), 4.56-4.57 (m, 1H), 4.73-4.74 (m, 1H), 5.53 (br s, 1H), 6.46 (t, J=73.2 Hz, 1H), 6.95-7.04 (m, 3H), 7.52 (s, 1H), 8.99 (s, 1H); ESI-MS m/z [M+H]+ 490.4.

Example 41 (S)-2-(4-(4-(difluoromethoxy)-2-fluorophenoxy)piperidin-1-yl)-7-methyl-N-(tetrahydrofuran-3-yl)pyrido[3,4-b]pyrazin-3-amine

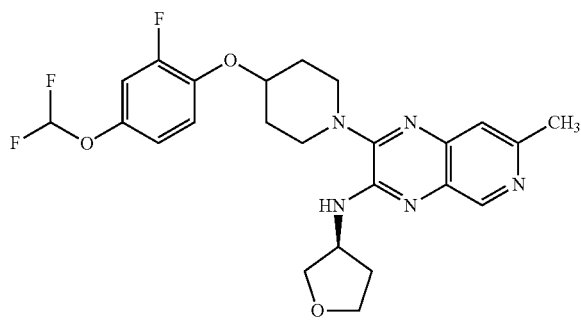

The title compound was prepared and purified in a manner similar to Example 38 using (S)-tetrahydrofuran-3-amine hydrochloride to give the title compound (17.5% yield) as a yellow film. 1H NMR (400 MHz, CDCl3) δ ppm 1.95-2.12 (m, 5H), 2.35-2.45 (m, 1H), 2.80 (s, 3H), 3.62-3.77 (m, 2H), 3.88-3.95 (m, 6H), 4.56-4.57 (m, 1H), 4.73-4.74 (m, 1H), 5.51 (br s, 1H), 6.46 (t, J=73.3 Hz, 1H), 6.96-7.02 (m, 3H), 7.53 (s, 1H), 8.98 (s, 1H); ESI-MS m/z [M+H]+ 490.4.

Example 42 2-(4-(2-fluoro-4-methoxybenzyl)piperazin-1-yl)-N-isopropyl-7-methylpyrido[3,4-b]pyrazin-3-amine

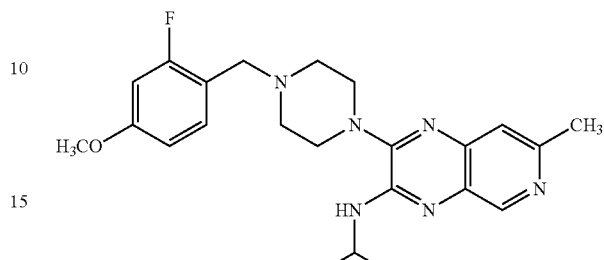

The title compound was prepared in a manner similar to Example 38 using propan-2-amine and 3-chloro-2-(4-(2-fluoro-4-methoxybenzyl)piperazin-1-yl)-7-methylpyrido[3,4-b]pyrazine. The title compound was purified by HPLC using Method B to give its free base (25.6% yield) as a yellow semi-solid. 1H NMR (400 MHz, CDCl3) δ ppm 1.31 (d, J=6.35 Hz, 6H), 2.63 (s, 3H), 2.66-2.68 (m, 4H), 3.34-3.36 (m, 4H), 3.62 (s, 2H), 3.81 (s, 3H), 4.32-4.36 (m, 1H), 4.98-5.00 (m, 1H), 6.63 (dd, J=11.72, 2.44 Hz, 1H), 6.70 (dd, J=8.79, 2.44 Hz, 1H), 7.26-7.32 (m, 1H) 7.36 (s, 1H), 8.89 (s, 1H); ESI-MS m/z [M+H]+ 425.4.

Example 43 N-cyclopropyl-2-(4-(2-fluoro-4-methoxy benzyl)piperazin-1-yl)-7-methylpyrido[3,4-b]pyrazin-3-amine

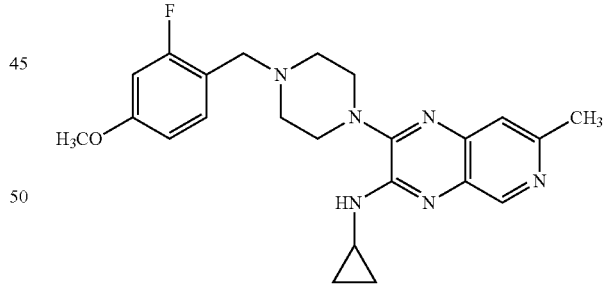

The title compound was prepared in a manner similar to Example 38 using cyclopropanamine and 3-chloro-2-(4-(2-fluoro-4-methoxy benzyl)piperazin-1-yl)-7-methylpyrido[3,4-b]pyrazine. The title compound was purified by HPLC using Method B to give its free base (19.8% yield) as a white solid. 1H NMR (400 MHz, CDCl3) δ ppm 0.59-0.61 (m, 2H), 0.92-0.94 (m, 2H), 2.66 (s, 3H), 2.67-2.69 (m, 4H), 2.91-2.93 (m, 1H), 3.36-3.40 (m, 4H), 3.66 (s, 2H), 3.81 (s, 3H), 6.63 (dd, J=11.72, 2.44 Hz, 1H), 6.71 (dd, J=8.79, 2.44 Hz, 1H), 7.27-7.28 (m, 1H), 7.39 (s, 1H), 8.99 (s, 1H); ESI-MS m/z [M+H]+ 423.4.

Example 44 (R)-2-(4-(2-fluoro-4-methoxybenzyl)piperazin-1-yl)-7-methyl-N-(tetrahydrofuran-3-yl)pyrido[3,4-b]pyrazin-3-amine

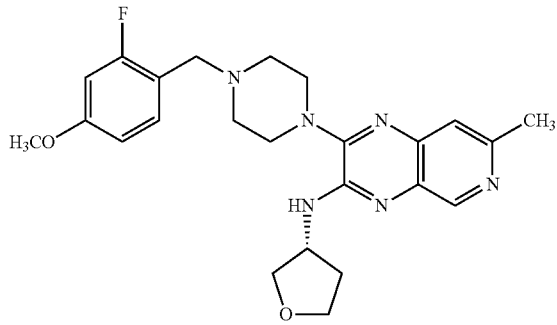 [SMILES: COc1ccc(CN2CCN(c3nc4cc(C)ncc4nc3N[C@@H]3CCOC3)CC2)c(F)c1]

The title compound was prepared in a manner similar to Example 38 using (R)-tetrahydrofuran-3-amine hydrochloride and 3-chloro-2-(4-(2-fluoro-4-methoxybenzyl)piperazin-1-yl)-7-methylpyrido[3,4-b]pyrazine. The title compound was purified by HPLC using Method B to give its free base (7.0% yield) as a yellow film. 1H NMR (400 MHz, CDCl3) δ ppm 1.91-1.92 (m, 1H), 2.43-2.45 (m, 1H), 2.65 (s, 3H), 2.67-2.70 (m, 4H), 3.39-3.43 (m, 4H), 3.79 (s, 2H), 3.81 (s, 3H), 3.85-3.87 (m, 2H), 4.01-4.02 (m, 2H), 4.72-4.74 (m, 1H), 5.23-5.24 (m, 1H), 6.63 (dd, J=11.72, 2.44 Hz, 1H), 6.69-6.72 (M, 1H), 7.27-7.28 (m, 1H), 7.39 (s, 1H), 8.91 (s, 1H); ESI-MS m/z [M+H]+ 453.4.

Example 45 (S)-2-(4-(2-fluoro-4-methoxy benzyl)piperazin-1-yl-7-methyl-N-(tetrahydrofuran-3-yl)pyrido[3,4-b]pyrazin-3-amine

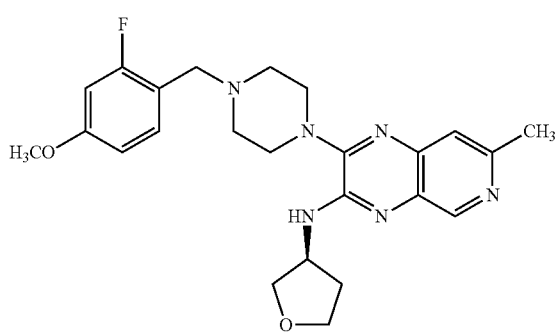 [SMILES: COc1ccc(CN2CCN(c3nc4cc(C)ncc4nc3N[C@H]3CCOC3)CC2)c(F)c1]

The title compound was prepared in a manner similar to Example 38 using (S)-tetrahydrofuran-3-amine hydrochloride and 3-chloro-2-(4-(2-fluoro-4-methoxybenzyl)piperazin-1-yl)-7-methylpyrido[3,4-b]pyrazine. The title compound was purified by HPLC using Method B to give its free base (4.4% yield) as a yellow film. 1H NMR (400 MHz, CDCl3) δ ppm 1.90-1.92 (m, 1H), 2.42-2.43 (m, 1H), 2.66 (s, 3H), 2.67-2.70 (m, 4H), 3.41-3.45 (m, 4H), 3.79 (s, 2H), 3.81 (s, 3H), 3.85-3.87 (m, 2H), 4.01-4.02 (m, 2H), 4.72-4.74 (m, 1H), 5.23-5.24 (m, 1H), 6.63 (dd, J=11.72, 2.44 Hz, 1H), 6.69-6.72 (m, 1H), 7.27-7.28 (m, 1H), 7.39 (s, 1H), 8.92 (s, 1H); ESI-MS m/z [M+H]+ 453.4.

Example 46 2-(4-(4-(difluoromethoxy)-2-fluorobenzyl)piperazin-1-yl)-N-isopropyl-7-methylpyrido[3,4-b]pyrazin-3-amine

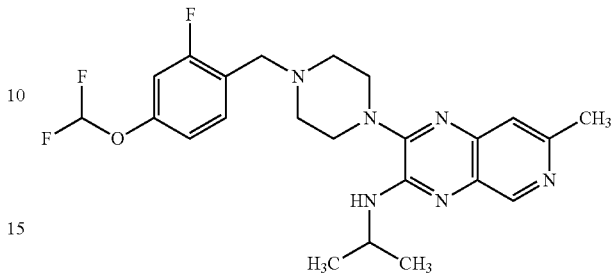

Combined 3-chloro-2-(4-(4-(difluoromethoxy)-2-fluorobenzyl)piperazin-1-yl)-7-methylpyrido[3,4-b]pyrazine (20.0 mg, 0.046 mmol), potassium fluoride (3.45 mg, 0.059 mmol), and DMSO (0.1 mL) then added N-ethyl-N-isopropylpropan-2-amine (0.032 mL, 0.183 mmol) and propan-2-amine (0.012 mL, 0.137 mmol) at 23° C. The reaction mixture was stirred at 23° C. for 1 h and then at 50° C. for 16 h. The reaction mixture was diluted with water (0.4 mL) to furnish a gummy solid. The mother liquor was decanted and the crude residue was purified by HPLC using Method B to give free base of title compound (2.9 mg, 13.79% yield) as a yellow solid. 1H NMR (400 MHz, DMSO-d6) δ ppm 1.23 (d, J=6.8 Hz, 6H), 2.51 (br. s., 3H), 2.57-2.70 (m, 4H), 3.35 (br. s., 4H), 3.60 (br. s., 2H), 4.26-4.36 (m, 1H), 6.33 (d, J=7.8 Hz, 1H), 7.04 (dd, J=8.5, 2.2 Hz, 1H), 7.13 (dd, J=10.7, 2.4 Hz, 1H), 7.15-7.45 (m, 2H), 7.50 (t, J=8.3 Hz, 1H), 8.66 (s, 1H); ESI-MS: m/z (M+H)+ 461.0.

Example 47 N-cyclopropyl-2-(4-(4-(difluoromethoxy)-2-fluorobenzyl)piperazin-1-yl)-7-methylpyrido[3,4-b]pyrazin-3-amine

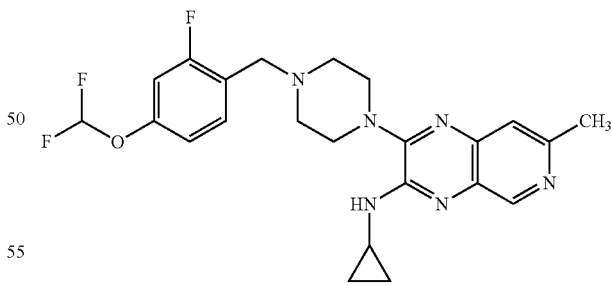

The title compound was prepared and purified in a manner similar to Example 46 using cyclopropanamine to give its free base (22.9% yield) as a yellow solid. 1H NMR (400 MHz, DMSO-d6) δ ppm 0.61-0.69 (m, 2H), 0.71-0.81 (m, 2H), 2.52 (s, 3H), 2.53-2.80 (m, 5H), 2.84 (tq, J=7.1, 3.6 Hz, 1H), 3.36 (br. s., 4H), 3.61 (br. s., 2H), 6.97 (br. s., 1H), 7.05 (dd, J=8.8, 2.0 Hz, 1H), 7.10-7.15 (m, 1H), 7.15-7.45 (m, 2H), 7.50 (t, J=8.5 Hz, 1H), 8.74 (s, 1H); ESI-MS: m/z (M+H)+ 459.0.

Example 48 (R)-2-(4-(4-(difluoromethoxy)-2-fluorobenzyl)piperazin-1-yl)-7-methyl-N-(tetrahydrofuran-3-yl)pyrido[3,4-b]pyrazin-3-amine

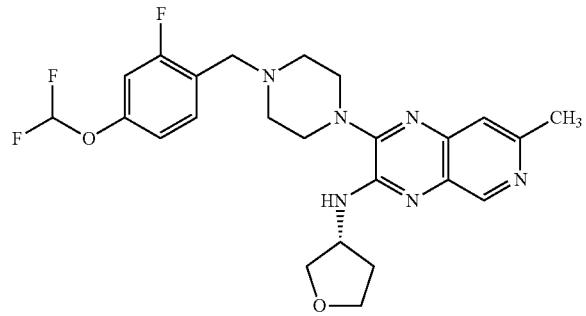 [SMILES: Cc1cc2nc(N3CCN(Cc4ccc(OC(F)F)cc4F)CC3)c(N[C@@H]3CCOC3)nc2cn1]

The title compound was prepared and purified in a manner similar to Example 46 using (R)-tetrahydrofuran-3-amine hydrochloride to give its free base (48.8% yield) as a yellow solid. 1H NMR (400 MHz, DMSO-d6) δ ppm 1.98-2.05 (m, 1H), 2.19-2.28 (m, 1H), 2.51 (s, 3H), 2.57-2.67 (m, 4H), 3.33-3.45 (m, 4H), 3.59 (s, 2H), 3.65 (dd, J=8.8, 4.4 Hz, 1H), 3.74 (td, J=8.1, 6.3 Hz, 1H), 2.50 (d, J=2.0 Hz, 1H), 3.97 (dd, J=8.8, 6.3 Hz, 1H), 4.51-4.59 (m, 1H), 6.67 (d, J=5.9 Hz, 1H), 7.04 (dd, J=8.5, 2.2 Hz, 1H), 7.12 (dd, J=10.7, 2.4 Hz, 1H), 7.14-7.45 (m, 2H), 7.50 (t, J=8.3 Hz, 1H), 8.68 (s, 1H); ESI-MS: m/z (M+H)+ 489.0.

Example 49 (S)-2-(4-(4-(difluoromethoxy)-2-fluorobenzyl)piperazin-1-yl)-7-methyl-N-(tetrahydrofuran-3-yl)pyrido[3,4-b]pyrazin-3-amine

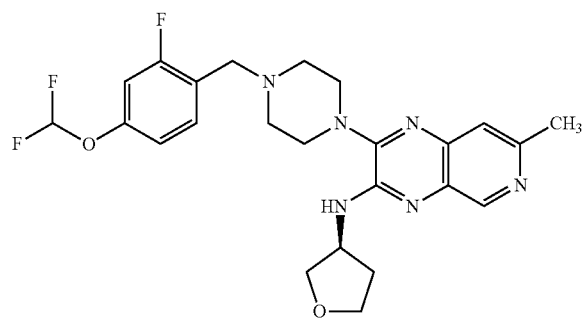 [SMILES: Cc1cc2nc(N3CCN(Cc4ccc(OC(F)F)cc4F)CC3)c(N[C@H]3CCOC3)nc2cn1]

The title compound was prepared and purified in a manner similar to Example 46 using (S)-tetrahydrofuran-3-amine hydrochloride to give its free base (46.2% yield) as a yellow solid. 1H NMR (400 MHz, DMSO-d6) δ ppm 1.96-2.06 (m, 1H), 2.18-2.30 (m, 1H), 2.51 (s, 3H), 2.56-2.71 (m, 4H), 3.33-3.48 (m, 4H), 3.59 (s, 2H), 3.63-3.68 (m, 1H), 3.74 (td, J=8.2, 6.1 Hz, 1H), 3.83-3.91 (m, 1H), 3.97 (dd, J=8.8, 6.3 Hz, 1H), 4.50-4.60 (m, 1H), 6.69 (d, J=5.9 Hz, 1H), 7.04 (dd, J=8.3, 2.4 Hz, 1H), 7.13 (dd, J=10.7, 2.4 Hz, 1H), 7.14-7.46 (m, 2H), 7.50 (t, J=8.5 Hz, 1H), 8.68 (s, 1H); ESI-MS: m/z (M+H)+489.0.

Example 50 2-(4-(2,4-difluorobenzyl)piperazin-1-yl)-7-methyl-N-(oxetan-3-yl)pyrido[3,4-b]pyrazin-3-amine

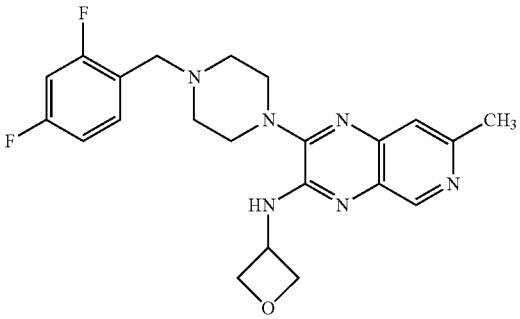 [SMILES: Cc1cc2nc(N3CCN(Cc4ccc(F)cc4F)CC3)c(NC3COC3)nc2cn1]

Combined 3-chloro-2-(4-(2,4-difluorobenzyl)piperazin-1-yl)-7-methylpyrido[3,4-b]pyrazine (20 mg, 0.051 mmol), potassium fluoride (3.87 mg, 0.067 mmol), and DMSO (0.1 mL) was added N-ethyl-N-isopropylpropan-2-amine (0.018 mL, 0.103 mmol) and oxetan-3-amine (10.71 μl, 0.154 mmol) at 23° C. The reaction mixture was stirred at 23° C. for 48 h. Additional portions of DMSO (0.1 mL) and oxetan-3-amine (7.14 μl, 0.103 mmol) were added to the reaction mixture which was stirred for an additional 15 h at 23° C. The reaction mixture was diluted with water (0.8 mL) and the crude product was extracted with EtOAc (2.0 mL). The organic layer was separated, washed with brine (1 mL), dried over Na2SO4, filtered, rinsed with EtOAc, and dried in vacuo. The crude material was purified by flash column chromatography using a gradient of 10-100% EtOAc in heptane to provide the free base of the title compound (9.1 mg, 41.6% yield) as a yellow solid. 1H NMR (400 MHz, DMSO-d6) δ ppm 2.51 (br. s., 3H), 2.63 (t, J=4.6 Hz, 4H), 3.43 (br. s., 4H), 3.60 (s, 2H), 4.62 (t, J=6.3 Hz, 2H), 4.82 (t, J=6.8 Hz, 2H), 4.91-5.02 (m, 1H), 7.09 (td, J=8.5, 2.4 Hz, 1H), 7.23 (td, J=9.9, 2.7 Hz, 1H), 7.32 (s, 1H), 7.38 (d, J=4.9 Hz, 1H), 7.46-7.54 (m, 1H), 8.64 (s, 1H); ESI-MS: m/z (M+H)+ 427.0.

The compounds of the invention can be administered alone or in the form of a pharmaceutical composition. In practice, the compounds of the invention are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including orally, in particular by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the present invention may be varied depending upon its particular form and may conveniently be between 1% to about 50% of the weight of the unit dose form. The term "pharmaceutically acceptable excipient" refers to those typically used in preparing pharmaceutical compositions and should be pharmaceutically pure and non-toxic in the amounts used. They generally are a solid, semi-solid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dose form, each dose typically containing from about 0.5 mg to about 100 mg of a compounds of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage on a daily schedule.

In one particular variation, the composition is a pharmaceutical composition adapted for oral administration, such as a tablet or a capsule or a liquid formulation, for example, a solution or suspension, adapted for oral administration. In still another particular variation, the pharmaceutical composition is a liquid formulation adapted for parenteral administration.

Compounds of the present invention are modulators of GPR6, and as such are useful in the treatment and prevention of conditions associated with GPR6. As mentioned above, the major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors. GPR6 is enriched in D2 receptor expressing MSNs in the striatum where GPR6 activity is functionally opposed to D2 receptor signaling. Antagonism or inverse agonism of Gs coupled GPR6 decreases cAMP in MSNs and provides a functional alternative to dopamine mediated activation of D2 receptors.

Antagonism or inverse agonism of Gs coupled GPR6 provides a functional alternative to dopamine mediated activation of D2 receptors. As such, compounds that modulate the activity of GPR6 are useful for treating in a variety of neurological and psychiatric disorders. For example movement disorders including Parkinson's disease and Huntington's disease either alone or in combination with other agents are approved for the treatment of Parkinson's disease including L-DOPA, dopaminergic agonists, MAO B inhibitors, DOPA decarboxylase inhibitors and C(O)MT inhibitors. Other disease indications that could be treated by modulation of GPR6 include drug addiction and eating disorders, cognitive disorders, schizophrenia, bipolar disorders, and depression.

In another embodiment, the invention provides methods of treating conditions associated with GPR6, comprising: administering to a patient in need thereof an effective amount of a compound of the invention. In another embodiment, a compound of the invention is provided for use as a medicament. The invention also provides the use of a compound of the invention, including the use for the manufacture of a medicament, to treat the conditions associated with GPR6 described herein. The compounds of the present invention are useful as GPR6 modulators for a variety of subjects (e.g., humans, non-human mammals and non-mammals).

As used herein terms "condition," "disorder," and "disease" relate to any unhealthy or abnormal state. The term "conditions associated with GPR6" includes conditions, disorders, and diseases in which the modulators of GPR6 provides a therapeutic benefit, such as Parkinson's disease, levodopa induced dyskinesias, and Huntington's disease, drug addiction, eating disorders, cognitive disorders, schizophrenia, bipolar disorders, and depression.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to, the species of patient, its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 1 mg to 200 mg. Specific amounts can be determined by the skilled person. Although these dosages are based on an average human subject having a mass of about 60 kg to about 70 kg, the physician will be able to determine the appropriate dose for other patients.

The pathological hallmark of Parkinson disease (PD) is neuronal cell loss within the substantia nigra. Degeneration of the nigrostriatal pathway causes reduction in the striatal concentration of dopamine which results in motor and nonmotor clinical manifestations. Many Parkinson's disease patients are treated with levodopa, a prodrug for dopamine. Levodopa has common serious side effects including induced dyskinesia (LID), impulsive control disorders (ICD), psychotic symptoms and sleep disturbances. LID is progressive (90% of PD patients develop LID within 10 yrs). Irreversible adaptations occur in D1 receptor signaling in MSNs in rodent models of LID including reduced desensitization leading to hypersensitivity in the direct pathway. Genetic inactivation of D1 but not D2 receptors abolishes LID in mice. However blockade of D1 receptor signaling does not affect the antiparkinsonian efficacy of L-DOPA.

In a particular embodiment, the present invention provides a method of treating Parkinson's disease comprising: administering to a patient in need thereof an effective amount of a compound of the invention. That is, the invention also provides the use of a compound of the invention, including the use for the manufacture of a medicament, to treat Parkinson's disease.

The compounds of the invention may be combined with one or more other pharmacologically active compounds or therapies for the treatment of one or more disorders, diseases or conditions for which GPR6 is indicated may be administered simultaneously, sequentially or separately in combination with one or more compounds or therapies for treating Parkinson's disease, levodopa induced dyskinesias, and Huntington's disease, drug addiction, eating disorders, cognitive disorders, schizophrenia, bipolar disorders, and depression. Such combinations may offer significant therapeutic advantages, including fewer side effects, improved ability to treat underserved patient populations, or synergistic activity. In particular, the compounds of the invention may be administered with levodopa for treating Parkinson's disease. The present invention provides a method treating Parkinson's disease comprising: administering to a patient in need thereof an effective amount of a compound of the invention in combination with levadopa. The invention also provides the use of a compound of the invention in combination with levadopa, including the use for the manufacture of a medicament, to treat Parkinson's disease.

The activity of compounds as GPR6 modulators may be determined by a variety of methods, including in vitro and in vivo methods.

Example A

Inhibition of cAMP Activity of GPR6 In Vitro Assay

This cell based assay measures the ability of compounds to inhibit the constitutive cAMP activity of GPR6 receptor expressed in CHO-K1 cells. CHO cells were stably expressed with GPR6 receptor, whose expression is controlled by a tetracycline inducable element. The cells were cultured in medium containing F12K, 10% FBS, 1% Penn/Strep, 200 ug/mL Hygromycin. GPR6 receptor expression was induced for 20 hrs with 2 □g/ml doxycycline (sigma D9891) in growth media. After addition of doxycycline cells were plated at a density of 450-750 cells per well in 96-well half-volume black tissue culture plates (Costar) and placed in an incubator (37°, 5% CO2) for 20 hours prior to cAMP assays.

Culture media was removed from cells and they were washed with 50 □L/well of Ringer's Buffer (MgCl2 0.047 mg/mL, NaH2PO4 0.18 mg/mL, Na2HPO4 0.1 mg/mL, KCl 0.34 mg/mL, NaHCO3 1.26 mg/mL, D-glucose 1.8 mg/mL, NaCl 7 mg/mL; pH=7.4). Compounds suspended in DMSO were diluted in Ringer's Buffer containing 0.5% fatty acid free BSA plus 300 μM IBMX and incubated on cells for 45 min at 37° and 5% CO2. After incubation cells were incubated for 10 min at room temp with Eu-cAMP tracer solution from a Perkin Elmer Lance HTRF Ultra cAMP assay kit (TRF0263). Then ULight™-anti-cAMP solution from the Lance HTRF kit was added and incubated on a shaker at room temp for 1 hour prior to HTRF detection in a Perkin Elmer Envision plate reader.

IC50 curves were generated with a four-parameter logistic equation using GraphPad Prism 5.03. Measured EC50 value (nM) of example compounds in this assay is provided in the Table 1 below.

TABLE 1

| Ex. | EC50 (nM) |
|---|---|
| 1 | 59.4 |
| 2 | 16.5 |
| 3 | 88.2 |
| 4 | 49.6 |
| 5 | 30.1 |
| 7 | |
| 6 | 47.9 |
| 8 | 18.5 |
| 9 | 52.3 |
| 10 | 69.3 |
| 11 | 61.4 |
| 12 | 49.4 |
| 13 | 48.2 |
| 14 | 75.2 |
| 15 | 21.9 |
| 16 | |
| 17 | |
| 18 | 39.9 |
| 19 | 62.6 |
| 20 | 81.4 |
| 21 | 162.2 |
| 22 | 37.3 |
| 23 | 158.1 |
| 24 | 311.2 |
| 25 | 277.8 |
| 26 | 466.2 |
| 27 | 446.3 |
| 28 | >1000 |
| 29 | >1000 |
| 30 | 80.1 |
| 31 | 188 |
| 32 | 326 |
| 33 | 101.7 |
| 34 | 94.9 |
| 35 | 66.4 |
| 36 | 76.3 |
| 37 | 128 |
| 38 | 309 |
| 39 | >5000 |
| 40 | >1000 |
| 41 | >1000 |
| 42 | 275.6 |
| 43 | >1000 |
| 44 | >1000 |
| 45 | >1000 |
| 46 | >1000 |
| 47 | >1000 |

TABLE 1-continued

| Ex. | EC50 (nM) |
|---|---|
| 48 | >1000 |
| 49 | >1000 |
| 50 | 163.7 |

Example B

Haloperidol-Induced Catalepsy—In Vivo Rodent Parkinson's Disease Model

The motor symptoms of Parkinson's disease include akinesia, bradykinesia, rigidity, tremor and postural abnormalities and are associated with the loss of nigral dopaminergic cells and a decline in striatal dopamine levels. Administration of haloperidol to rodents leads to a transient parkinsonian-like state that is reversed by the administration of L-Dopa (Duty, S.; Jenner, P. Br. J. Pharmacol. (2011), 164, 1357-1391) and other drugs that have been clinically validated for the treatment of Parkinson's disease. Haloperidol antagonizes dopamine D2 and, to a lesser extent, D1 receptors in medium spiny neurons that comprise the indirect and direct pathways of the motor circuit respectively. The resultant block of striatal dopamine transmission results in abnormal downstream firing within the basal ganglia circuits that is manifest as symptoms of muscle rigidity and catalepsy. Catalepsy has been postulated to reflect the clinical features of Parkinson's disease, whereby patients experience an inability of to initiate movements.

Male Sprague-Dawley rats (Charles River, Calco, Italy) weighing 175-200 g are used. Alternatively, male C57Bl6 mice weighing 25-35 g were used. The cataleptic state was induced by the subcutaneous administration of the dopamine receptor antagonist haloperidol (0.3 mg/kg, sc), 90 min before testing the animals on the vertical grid test. For this test, the rats or mice were placed on the wire mesh cover of a 25 cm×43 cm plexiglass cage placed at an angle of about 70 degrees with the bench table. The subject was placed on the grid with all four legs abducted and extended ("frog posture"). The use of such an unnatural posture is essential for the specificity of this test for catalepsy. The time span from placement of the paws until the first complete removal of one paw (descent latency) was measured maximally for 120 sec for rats. For mice, the front paws of a mouse was placed on a horizontal metal bar raised 2" above a Plexiglas platform and time was recorded for up to 30 seconds per trial. The test ended when the animal's front paws returned to the platform or after 30 seconds. The test was repeated three times and the average of the three trials was reported as the intensity index of catalepsy.

Catalepsy was measured 30 min, 90 min, and/or 90 min after dosing the subjects a 1.0 mg/kg i.p. dose of haloperidol along with the GPR6 modulator test compound. Test compound plasma and brain levels were determined by collected tissue samples at the end of the experiment, which was either at the 120 or 240 min time point. A representative number of compounds of the invention were administered in a dose range from 0.1 to 100 mg/kg i.p, sc or po in conjunction with haloperidol. The A2a antagonist KW6002 (istradefylline) was dosed at 0.6 mg/kg i.p. as a positive control.

Measured % reversal of example compounds in this assay is provided in the Table 2 below.

TABLE 2

| Ex. | Species | Dose (mg/kg) | Route | % reversal at 90 min |
|---|---|---|---|---|
| 7 | Rat | 1 | sc | 33.5 |
| 7 | Rat | 10 | sc | 63.6 |
| 7 | Rat | 30 | sc | 42.8 |

*-significantly different than vehicle contol, one-way ANOVA with Bonferroni's multiple test correction.

What is claimed is:
1. A compound of the formula

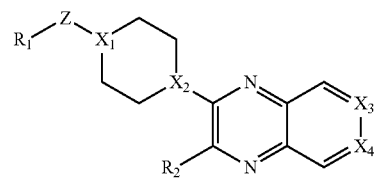

I or a pharmaceutically acceptable salt thereof, wherein
$R_1$ is phenyl optionally substituted with 1 to 5 substituents independently selected from the group consisting of $C_{1-4}$ alkyl, $C_{1-4}$ alkoxy, cyano, and halo, wherein the $C_{1-4}$ alkyl and $C_{1-4}$ alkoxy $R_1$ substituents are optionally substituted with 1 to 6 substituents independently selected from the group consisting of halo;
$X_1$ is N and $X_2$ is CH; or
$X_1$ is CH and $X_2$ is N; or
$X_1$ is N and $X_2$ is N;
when $X_1$ is N, Z is $C_{1-6}$ alkylene;
when $X_1$ is CH, Z is $C_{1-6}$ alkylene and;
$R_2$ is $NR_6R_7$;
$R_6$ is selected from the group consisting of hydrogen and $C_{1-6}$ alkyl;
$R_7$ is selected from the group consisting of $C_{1-6}$ alkyl, $C_{3-8}$ cycloalkyl which is optionally substituted with halo or hydroxy, and $C_{3-6}$ heterocyclyl;
$X_3$ is $CCH_3$ and $X_4$ is N; or
$X_3$ is N and $X_4$ is $CCH_3$;
excluding the compounds:
N-cyclopropyl-3-(4-(2,4-difluorobenzyl)piperazin-1-yl)-7-methylpyrido[3,4-b]pyrazin-2-amine;
3-(4-(5-chloro-2-fluorobenzyl)piperazin-1-yl)-N-cyclopropyl-7-methylpyrido[3,4-b]pyrazin-2-amine;
N-cyclopropyl-3-(4-(2,4-difluorobenzyl)piperidin-1-yl)-7-methylpyrido[3,4-b]pyrazin-2-amine;
N-cyclopropyl-2-(4-(2,4-difluorobenzyl)piperidin-1-yl)-7-methylpyrido[3,4-b]pyrazin-3-amine;
N-cyclopropyl-3-(4-(2,4-difluorophenoxy)piperidin-1-yl)-7-methylpyrido[3,4-b]pyrazin-2-amine;
3-(4-(4-chloro-2-fluorophenoxy)piperidin-1-yl)-N-cyclopropyl-7-methylpyrido[3,4-b]pyrazin-2-amine; and
N-cyclopropyl-3-(1-(2,4-difluorobenzyl)piperidin-4-yl)-7-methylpyrido[3,4-b]pyrazin-2-amine.

2. The compound or pharmaceutically acceptable salt thereof according to claim 1, wherein $X_1$ is CH and $X_2$ is N.

3. The compound or pharmaceutically acceptable salt thereof according to claim 1, wherein $X_1$ is N and $X_2$ is N.

4. The compound or pharmaceutically acceptable salt thereof according to claim 3, wherein $X_3$ is $CCH_3$ and $X_4$ is N.

5. The compound or pharmaceutically acceptable salt thereof according to claim 1, wherein Z is $C_{1-6}$ alkylene.

6. The compound or pharmaceutically acceptable salt thereof according to claim 1, wherein Z is —O—.

7. The compound according to claim 1, which is selected from the group consisting of:

3-(4-(2,4-difluorobenzyl)piperazin-1-yl)-N-isopropyl-7-methylpyrido[3,4-b]pyrazin-2-amine;
3-(4-(2,4-difluorophenoxy)piperidin-1-yl)-N-isopropyl-7-methylpyrido[3,4-b]pyrazin-2-amine;
(S)-3-(4-(2,4-difluorobenzyl)piperazin-1-yl)-7-methyl-N-(tetrahydrofuran-3-yl)pyrido[3,4-b]pyrazin-2-amine;
(S)-3-(4-(2,4-difluorophenoxy)piperidin-1-yl)-7-methyl-N-(tetrahydrofuran-3-yl)pyrido[3,4-b]pyrazin-2-amine;
(R)-3-(4-(2,4-difluorophenoxy)piperidin-1-yl)-7-methyl-N-(tetrahydrofuran-3-yl)pyrido[3,4-b]pyrazin-2-amine;
(R)-3-(4-(2,4-difluorobenzyl)piperazin-1-yl)-7-methyl-N-(tetrahydrofuran-3-yl)pyrido[3,4-b]pyrazin-2-amine;
N-cyclopropyl-3-(4-(2-fluoro-4-methoxyphenoxy)piperidin-1-yl)-7-methylpyrido[3,4-b]pyrazin-2-amine;
cis-3-((3-(4-(2,4-difluorophenoxy)piperidin-1-yl)-7-methylpyrido[3,4-b]pyrazin-2-yl)amino)cyclobutanol;
cis-3-((3-(4-(2,4-difluorobenzyl)piperazin-1-yl)-7-methylpyrido[3,4-b]pyrazin-2-yl)amino)cyclobutanol;
trans-3-(4-(2,4-difluorophenoxy)piperidin-1-yl)-N-(3-fluorocyclobutyl)-7-methylpyrido[3,4-b]pyrazin-2-amine;
trans-3-(4-(2,4-difluorobenzyl)piperazin-1-yl)-N-(3-fluorocyclobutyl)-7-methylpyrido[3,4-b]pyrazin-2-amine;
trans-3-((3-(4-(2,4-difluorophenoxy)piperidin-1-yl)-7-methylpyrido[3,4-b]pyrazin-2-yl)amino)cyclobutanol;
trans-3-((3-(4-(2,4-difluorobenzyl)piperazin-1-yl)-7-methylpyrido[3,4-b]pyrazin-2-yl)amino)cyclobutanol;
3-(4-(2,4-difluorobenzyl)piperazin-1-yl)-7-methyl-N-(oxetan-3-yl)pyrido[3,4-b]pyrazin-2-amine;
3-(4-(2,4-difluorophenoxy)piperidin-1-yl)-7-methyl-N-(oxetan-3-yl)pyrido[3,4-b]pyrazin-2-amine;
3-(4-(4-(difluoromethoxy)-2-fluorophenoxy)piperidin-1-yl)-7-methyl-N-(oxetan-3-yl)pyrido[3,4-b]pyrazin-2-amine;
3-(4-(4-(difluoromethoxy)-2-fluorophenoxy)piperidin-1-yl)-N-isopropyl-7-methylpyrido[3,4-b]pyrazin-2-amine;
N-cyclopropyl-3-(4-(4-(difluoromethoxy)-2-fluorophenoxy)piperidin-1-yl)-'7-methylpyrido[3,4-b]pyrazin-2-amine;
(R)-3-(4-(4-(difluoromethoxy)-2-fluorophenoxy)piperidin-1-yl)-7-methyl-N-(tetrahydrofuran-3-yl)pyrido[3,4-b]pyrazin-2-amine;
(S)-3-(4-(4-(difluoromethoxy)-2-fluorophenoxy)piperidin-1-yl)-7-methyl-N-(tetrahydrofuran-3-yl)pyrido[3,4-b]pyrazin-2-amine;
3-(4-(2-fluoro-4-methoxybenzyl)piperazin-1-yl)-N-isopropyl-7-methylpyrido[3,4-b]pyrazin-2-amine;
N-cyclopropyl-3-(4-(2-fluoro-4-methoxybenzyl)piperazin-1-yl)-7-methylpyrido[3,4-b]pyrazin-2-amine;
(R)-3-(4-(2-fluoro-4-methoxybenzyl)piperazin-1-yl)-7-methyl-N-(tetrahydrofuran-3-yl)pyrido[3,4-b]pyrazin-2-amine;
(S)-3-(4-(2-fluoro-4-methoxybenzyl)piperazin-1-yl)-7-methyl-N-(tetrahydrofuran-3-yl)pyrido[3,4-b]pyrazin-2-amine;
3-(4-(4-(difluoromethoxy)-2-fluorobenzyl)piperazin-1-yl)-N-isopropyl-7-methylpyrido[3,4-b]pyrazin-2-amine;
N-cyclopropyl-3-(4-(4-(difluoromethoxy)-2-fluorobenzyl)piperazin-1-yl)-'7-methylpyrido[3,4-b]pyrazin-2-amine;
(R)-3-(4-(4-(difluoromethoxy)-2-fluorobenzyl)piperazin-1-yl)-7-methyl-N-(tetrahydrofuran-3-yl)pyrido[3,4-b]pyrazin-2-amine;
(S)-3-(4-(4-(difluoromethoxy)-2-fluorobenzyl)piperazin-1-yl)-7-methyl-N-(tetrahydrofuran-3-yl)pyrido[3,4-b]pyrazin-2-amine;
2-(4-(2,4-difluorobenzyl)piperazin-1-yl)-N-isopropyl-7-methylpyrido[3,4-b]pyrazin-3-amine;
N-cyclopropyl-2-(4-(2,4-difluorobenzyl)piperazin-1-yl)-7-methylpyrido[3,4-b]pyrazin-3-amine;
(S)-2-(4-(2,4-difluorobenzyl)piperazin-1-yl)-7-methyl-N-(tetrahydrofuran-3-yl)pyrido[3,4-b]pyrazin-3-amine;
(R)-2-(4-(2,4-difluorobenzyl)piperazin-1-yl)-7-methyl-N-(tetrahydrofuran-3-yl)pyrido[3,4-b]pyrazin-3-amine;
N-cyclopropyl-2-(4-(2,4-difluorophenoxy)piperidin-1-yl)-7-methylpyrido[3,4-b]pyrazin-3-amine;
2-(4-(2,4-difluorophenoxy)piperidin-1-yl)-N-isopropyl-7-methylpyrido[3,4-b]pyrazin-3-amine;
(R)-2-(4-(2,4-difluorophenoxy)piperidin-1-yl)-7-methyl-N-(tetrahydrofuran-3-yl)pyrido[3,4-b]pyrazin-3-amine;
(S)-2-(4-(2,4-difluorophenoxy)piperidin-1-yl)-7-methyl-N-(tetrahydrofuran-3-yl)pyrido[3,4-b]pyrazin-3-amine;
2-(4-(4-(difluoromethoxy)-2-fluorophenoxy)piperidin-1-yl)-N-isopropyl-7-methylpyrido[3,4-b]pyrazin-3-amine;
N-cyclopropyl-2-(4-(4-(difluoromethoxy)-2-fluorophenoxy)piperidin-1-yl)-'7-methylpyrido[3,4-b]pyrazin-3-amine;
(R)-2-(4-(4-(difluoromethoxy)-2-fluorophenoxy)piperidin-1-yl)-7-methyl-N-(tetrahydrofuran-3-yl)pyrido[3,4-b]pyrazin-3-amine;
(S)-2-(4-(4-(difluoromethoxy)-2-fluorophenoxy)piperidin-1-yl)-7-methyl-N-(tetrahydrofuran-3-yl)pyrido[3,4-b]pyrazin-3-amine;
2-(4-(2-fluoro-4-methoxybenzyl)piperazin-1-yl)-N-isopropyl-7-methylpyrido[3,4-b]pyrazin-3-amine;
N-cyclopropyl-2-(4-(2-fluoro-4-methoxybenzyl)piperazin-1-yl)-7-methylpyrido[3,4-b]pyrazin-3-amine;
(R)-2-(4-(2-fluoro-4-methoxybenzyl)piperazin-1-yl)-7-methyl-N-(tetrahydrofuran-3-yl)pyrido[3,4-b]pyrazin-3-amine;
(S)-2-(4-(2-fluoro-4-methoxybenzyl)piperazin-1-yl)-7-methyl-N-(tetrahydrofuran-3-yl)pyrido[3,4-b]pyrazin-3-amine;
2-(4-(4-(difluoromethoxy)-2-fluorobenzyl)piperazin-1-yl)-N-isopropyl-7-methylpyrido[3,4-b]pyrazin-3-amine;
N-cyclopropyl-2-(4-(4-(difluoromethoxy)-2-fluorobenzyl)piperazin-1-yl)-'7-methylpyrido[3,4-b]pyrazin-3-amine;
(R)-2-(4-(4-(difluoromethoxy)-2-fluorobenzyl)piperazin-1-yl)-7-methyl-N-(tetrahydrofuran-3-yl)pyrido[3,4-b]pyrazin-3-amine;
(S)-2-(4-(4-(difluoromethoxy)-2-fluorobenzyl)piperazin-1-yl)-7-methyl-N-(tetrahydrofuran-3-yl)pyrido[3,4-b]pyrazin-3-amine; and
2-(4-(2,4-difluorobenzyl)piperazin-1-yl)-7-methyl-N-(oxetan-3-yl)pyrido[3,4-b]pyrazin-3-amine;

or a pharmaceutically acceptable salt of any one of the above-mentioned compounds.

8. A pharmaceutical composition comprising a compound or pharmaceutically acceptable salt thereof as defined in claim 1, and a pharmaceutically acceptable excipient.

* * * * *